United States Patent
Nettekoven et al.

(10) Patent No.: US 7,297,707 B2
(45) Date of Patent: Nov. 20, 2007

(54) BENZOTHIAZOLYL DERIVATIVES

(75) Inventors: Matthias Heinrich Nettekoven, Grenzach-Wyhlen (DE); Stephan Roever, Inzlingen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 32 days.

(21) Appl. No.: 10/871,952

(22) Filed: Jun. 18, 2004

(65) Prior Publication Data

US 2004/0266845 A1    Dec. 30, 2004

(30) Foreign Application Priority Data

Jun. 20, 2003    (EP)    ................... 03013403

(51) Int. Cl.
A01N 43/78    (2006.01)
A61K 31/425    (2006.01)
C07D 277/82    (2006.01)
(52) U.S. Cl. ...................... 514/367; 548/163
(58) Field of Classification Search ................ 514/367; 548/163
See application file for complete search history.

(56) References Cited

U.S. PATENT DOCUMENTS

| 3,940,418 | A | 2/1976 | Hamilton |
| 5,462,960 | A | 10/1995 | Barth et al. |
| 5,596,106 | A | 1/1997 | Cullinan et al. |
| 5,624,941 | A | 4/1997 | Barth et al. |
| 6,433,188 | B1 | 8/2002 | Corbett et al. |
| 6,441,184 | B1 | 8/2002 | Corbett et al. |
| 6,448,399 | B1 | 9/2002 | Corbett et al. |
| 6,545,155 | B2 | 4/2003 | Corbett et al. |

FOREIGN PATENT DOCUMENTS

| EP | 576357 | 6/1993 |
| EP | 0 604 657 A1 | 7/1994 |
| EP | 656 354 A1 | 11/1994 |
| EP | 656 354 B1 | 11/1994 |
| EP | 658 546 A1 | 12/1994 |
| EP | 658 546 B1 | 12/1994 |
| WO | WO96/02248 | 2/1996 |
| WO | WO97/19063 | 5/1997 |
| WO | WO 00/15609 | 3/2000 |
| WO | WO 00/46209 | 8/2000 |
| WO | WO 01/32663 | 5/2001 |
| WO | WO 01/64632 | 9/2001 |
| WO | WO 01/64633 | 9/2001 |
| WO | WO 01/64634 | 9/2001 |
| WO | WO 01/70700 | 9/2001 |
| WO | WO 02/28346 | 4/2002 |
| WO | WO 03/045386 A1 | 6/2003 |

OTHER PUBLICATIONS

Kurzer et al., Heterocyclic compounds from urea derivatives, (J. Chem. Soc., Abs. (1962), 230-6—XP-002296385).*
F. Barth, et al., "Cannabinoid antagonists: From research tools to potential new drugs." Abstracts of Papers, 222$^{nd}$ ASC National Meeting, Chicago, IL Aug. 26-30, 2001.
F.M. Casiano, et. al., NIDA Res. Monogr. 105 (1991) 295-6.
G. Colombo, et. al., Life Sci. 63 (8) (1998) L-113-PL117.
W.A. Devane, et. al., Science 258 (1992) 1946-9.
V. Di Marzo, et. al., Nature 410 (6830) 822-825.
V. Di Marzo, et. al, Trends in Neuroscience 21 (12) (1998) 521-8.
C. Felder, et. al., J. Pharmacol. Exp. Ther. 284 (1) (1998) 291-7.
C. Felder, et. al., Proc. Natl. Acad. Sci. USA 90 (16) (1993) 7656-60.
Y. Gaoni, et. al., J. Am. Chem. Soc., 86 (1964) 1646.
K. Hosohata, et. al., Life Sci. 61 (1997) 115-118.
M. Kanyonyo, et. al., Bioorg. Med. Chem. Lett. 9 (15) (1999) 2233-2236.
R. Mechoulam (Ed.) in "Cannabinoids as therapeutic Agents", (1986) p. 1-20, CRC Press.
S. Munro, et. al., Nature 365 (1993) 61-61.
F. Ooms, et. al., J. Med. Chem 45 (9) (2002) 1748-1756.
M. Pacheco, et. al., J. Pharmacol. Exp. Ther. 257 (1) (1991) 170-183.
R.G. Pertwee, Curr. Med. Chem., 6 (8) (1999) 635-664.
R.G. Pertwee, Life Sci. 56 (23-24) (1995) 1949-55.
R.G. Pertwee, Pharmaceut. Sci. 3 (11) (1997) 539-545.
C. Porter, et. al., Pharmacol. Ther., 90 (1) (2001) 45-60.
D. Shire, J. Biol. Chem. 270 (8) (1995) 3726-31.
C.M. Williams, et. al., Psychopharmacology 143 (3) (1999) 315-317.

(Continued)

Primary Examiner—Alton Pryor
(74) Attorney, Agent, or Firm—George W. Johnston; Dennis P. Tramaloni; Samuel H. Megerditchian

(57) ABSTRACT

The present invention relates to compounds of formula (I)

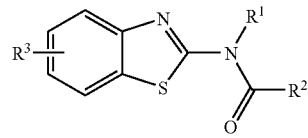

wherein $R^1$, $R^2$, $R^3$ $R^{3a}$ and $R^{3b}$ are as provided in the description, and pharmaceutically acceptable salts thereof, for use in the treatment and/or prophylaxis of diseases which are associated with the modulation of CB1 receptors such as obesity.

21 Claims, No Drawings

OTHER PUBLICATIONS

E.M. Williamson, et. al., Drugs 60 (6) (2000) 1303-1314.
Kurzer, Frederick et al, Journal of the Chemical Society, Abstracts 230-6 Coden: JCSAAZ; ISSN: 0590-9791 (1962).

Pertwee R.G., Pharmacolog and Therapeutics, XP002226467 vol. 74, No. 2, pp. 129-180 (1997).

* cited by examiner

BENZOTHIAZOLYL DERIVATIVES

BACKGROUND OF THE INVENTION

Two different subtypes of cannabinoid receptors ($CB_1$ amd $CB_2$) have been isolated and both belong to the G protein coupled receptor superfamily. An alternative spliced form of $CB_1$, $CB_{1A}$, has also been described, but it did not exhibit different properties in terms of ligand binding and receptor activation than $CB_1$ (D. Shire, C. Carrillon, M. Kaghad, B. Calandra, M. Rinaldi-Carmona, G. Le Fur, D. Caput, P. Ferrara, J. Biol. Chem. 270 (8) (1995) 3726-31). The $CB_1$ receptor is mainly located in the brain, whereas the $CB_2$ receptor is predominately distributed in the periphery and primarily localized in spleen and cells of the immune system (S. Munro, K. L. Thomas, M. Abu-Shaar, Nature 365 (1993) 61-65). Therefore in order to avoid side effects a $CB_1$-selective compound is desirable.

$\Delta^9$-tetrahydrocannabinol ($\Delta^9$-THC) is the principal psychoactive compound in the Indian hemp (Y. Gaoni, R. Mechoulam, J. Am. Chem. Soc., 86 (1964) 1646), *canabis savita* (marijuanan), which is used in medicine since ages (R. Mechoulam (Ed.) in "*Cannabinoids as therapeutic Agents*", 1986, pp. 1-20, CRC Press). $\Delta^9$-THC is a non-selective $CB_{1/2}$ receptor agonist and is available in the USA as dronabinol (marinol®) for the alleviation of cancer chemotherapy-induced emesis (CIE) and the reversal of body weight loss experienced by AIDS patients through appetite stimulation. In the UK Nabolinone (LY-109514, Cesamet®), a synthetic analogue of $\Delta^9$-THC, is used for CIE (R. G. Pertwee, Pharmaceut. Sci. 3 (11) (1997) 539-545, E. M. Williamson, F. J. Evans, Drugs 60 (6) (2000) 1303-1314). Anandamide (arachidonylethanolamide) was identified as the endogenous ligand (agonist) for the $CB_1$ receptor (R. G. Pertwee, Curr. Med. Chem., 6 (8) (1999) 635-664; W. A. Devane, L. Hanus, A. Breuer, R. G. Pertwee, L. A. Stevenson, G. Griffin, D. Gibson, A. Mandelbaum, A. Etinger, R. Mechoulam, Science 258 (1992) 1946-9). Anandamide and 2-arachidonoylglycerol (2-AG) modulate at the presynaptic nerve teminal negatively adenylate cyclase and voltage-sensitive $Ca^{2+}$ channels and activate the inwardly rectifying $K^+$ channel (V. Di Marzo, D. Melck, T. Bisogno, L. De Petrocellis, Trends in Neuroscience 21 (12) (1998) 521-8), thereby affecting neurotransmitter release and/or action, which decreases the release of neurotransmitter (A. C. Porter, C. C. Felder, Pharmacol. Ther., 90 (1) (2001) 45-60).

Anandamide as $\Delta^9$-THC also increases feeding through $CB_1$ receptor-mediated mechanism. $CB_1$ receptor selective antagonists block the increase in feeding associated with administration of anandamide (C. M. Williams, T. C. Kirkham, Psychopharmacology 143 (3) (1999) 315-317; C. C. Felder, E. M. Briley, J. Axelrod, J. T. Simpson, K. Mackie, W. A. Devane, Proc. Natl. Acad. Sci. U.S.A. 90 (16) (1993) 7656-60) and cause appetite suppression and weight loss (G. Colombo, R. Agabio, G. Diaz, C. Lobina, R. Reali, G. L. Gessa, Life Sci. 63 (8) (1998) L113-PL117).

Leptin is the primary signal through which the hypothalamus senses nutritional state and modulates food intake and energy balance. Following temporary food restriction, CB1 receptor knockout mice eat less than their wild-type litter-mates, and the CB1 antagonist SR141716A reduces food intake in wild-type but not knockout mice. Furthermore, defective leptin signaling is associated with elevated hypothalamic, but not cerebellar, levels of endocannabinoids in obese db/db and ob/ob mice and Zucker rats. Acute leptin treatment of normal rats and ob/ob mice reduces anandamide and 2-arachidonoyl glycerol in the hypothalamus. These findings indicate that endocannabinoids in the hypothalamus may tonically activate CB1 receptors to maintain food intake and form part of the neural circuitry regulated by leptin (V. Di Marzo, S. K. Goparaju, L. Wang, J. Liu, S. Bitkai, Z. Jarai, F. Fezza, G. I. Miura, R. D. Palmiter, T. Sugiura, G. Kunos, Nature 410 (6830) 822-825).

SR-141716A, a CB1 selective antagonist/inverse agonist is undergoing currently phase III clinical trials for the treatment of obesity. In a double blind placebo-controlled study, at the doses of 5, 10 and 20 mg daily, SR141716 significantly reduced body weight when compared to placebo (F. Barth, M. Rinaldi-Carmona, M. Arnone, H. Heshmati, G. Le Fur, "*Cannabinoid antagonists: From research tools to potential new drugs.*" Abstracts of Papers, 222nd ACS National Meeting, Chicago, Ill., United States, Aug. 26-30, 2001). Other compounds which have been proposed as CB1 receptor antagonists respectively inverse agonists are aminoalkylindols (AAI; M. Pacheco, S. R. Childers, R. Arnold, F. Casiano, S. J. Ward, J. Pharmacol. Exp. Ther. 257 (1) (1991) 170-183), like 6-bromopravadoline (WIN54661; F. M. Casiano, R. Arnold, D. Haycock, J. Kuster, S. J. Ward, NIDA Res. Monogr. 105 (1991) 295-6) or 6-iodopravadoline (AM630, K. Hosohata, R. M. Quock, R. M; Hosohata, T. H. Burkey, A. Makriyannis, P. Consroe, W. R. Roeske, H. I. Yamamura, Life Sci. 61 (1997) 115-118; R. Pertwee, G. Griffin, S. Fernando, X. Li, A. Hill, A. Makriyannis, Life Sci. 56 (23-24) (1995) 1949-55). Arylbenzo[b]thiophene and benzo[b]furan (LY320135, C. C. Felder, K. E. Joyce, E. M. Briley, M. Glass, K. P. Mackie, K. J. Fahey, G. J. Cullinan, D. C. Hunden, D. W. Johnson, M. O. Chaney, G. A. Koppel, M. Brownstein, J. Pharmacol. Exp. Ther. 284 (1) (1998) 291-7) as disclosed in WO9602248 or U.S. Pat. No. 5,596, 106, 3-alkyl-(5,5-diphenyl)-imidazolidine-diones (M. Kanyonyo, S. J. Govaerts, E. Hermans, J. H. Poupaert, D. M. Lambert, Bioorg. Med. Chem. Lett. 9 (15) (1999) 2233-2236.) as well as 3-alkyl-5-arylimidazolidine-diones (F. Ooms, J. Wouters, O. Oscaro. T. Happaerts, G. Bouchard, P.-A. Carrupt, B. Testa, D. M. Lambert, J. Med. Chem. 45 (9) (2002) 1748-1756) are known to antagonize the $CB_1$ receptor respectively to act as an inverse agonist on the $hCB_1$ receptor. WO0015609 (FR2783246-A1), WO0164634 (FR2805817-A1), WO0228346, WO0164632 (FR2805818-A1), WO0164633 (FR2805810-A1) discloses substituted 1-bis(aryl)methyl-azetidine derivatives as antagonists of $CB_1$. In WO0170700 4,5-dihydro-1H-pyrazole derivatives are described as $CB_1$ antagonists. In several patents bridged and non-bridged 1,5-diphenyl-3-pyrazolecarboxamide derivatives are disclosed as $CB_1$ antagonists/inverse agonists (WO0132663, WO0046209, WO9719063, EP658546, EP656354, U.S. Pat. No. 5,624,941, EP576357, U.S. Pat. No. 3,940,418).

SUMMARY OF THE INVENTION

It is an object of this invention to provide selective, directly acting CB1 receptor antagonists respectively inverse agonists. Such antagonists/inverse antagonists are useful in medical therapy, particularly in the treatment and/or prevention of diseases which are associated with the modulation of CB1 receptors. The present invention is useful in the treatment of obesity.

The present invention provides a compound of formula (I)

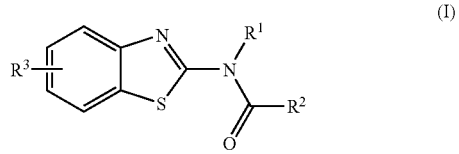

wherein
$R^1$ is phenyl, or phenyl mono-, di- or tri-substituted, independently, by a group selected from the group consisting of halogen, lower alkoxy, lower alkyl, halogenated-lower alkoxy and di-lower alkylamino;
$R^2$ is phenyl, or phenyl mono-, di- or tri-substituted, independently, by a group selected from the group consisting of halogen, halogenated-lower alkyl, nitro and cyano;
$R^3$ is hydrogen, lower alkyl, benzyl, lower alkoxy, halogen, cyano, nitro, amino, —NHSO$_2$—$R^{3a}$ or —NHCO—$R^{3b}$;
$R^{3a}$ is lower alkyl, di-lower alkylamino, benzyl, phenyl or phenyl mono-, di- or tri-substituted, independently, by lower alkyl;
$R^{3b}$ is benzyl, phenyl or phenyl mono-, di- or tri-substituted, independently, by lower alkyl;
or a pharmaceutically acceptable salt thereof.

DETAILED DESCRIPTION OF THE INVENTION

Unless otherwise indicated, the following definitions are set forth to illustrate and define the meaning and scope of the various terms used to describe the invention herein. In this specification the term "lower" is used to mean a group consisting of one to eight, preferably of one to six, and more preferably of one to four carbon atom(s).

The term "halogen" refers to fluorine, chlorine, bromine and iodine, preferably to chlorine and fluorine.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl", alone or in combination with other groups, refers to a branched or straight-chain monovalent alkyl radical of one to eight carbon atoms, preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "alkoxy" refers to the group R'—O—, wherein R' is alkyl. The term "lower alkoxy" refers to the group R'—O—, wherein R' is lower alkyl. Examples of lower alkoxy groups are e.g. methoxy, ethoxy, propoxy, isopropoxy, butoxy, isobutoxy and hexyloxy, with methoxy being especially preferred.

The term "di-lower alkylamino" refers to the group —N(R')R", wherein R' and R" are each independently a lower alkyl residue.

The term "halogenated lower alkyl" refers to a lower alkyl group wherein at least one of the hydrogens of the lower alkyl group is replaced by halogen, such as fluorine and chlorine, preferably fluorine. Among the preferred halogenated lower alkyl groups are trifluoromethyl, difluoromethyl, fluoromethyl and chloromethyl, with trifluoromethyl being especially preferred.

The term "halogenated lower alkoxy" refers to a lower alkoxy group wherein at least one of the hydrogens of the lower alkoxy group is replaced by halogen, such as fluorine or chlorine, preferably by fluorine. Among the preferred halogenated lower alkoxy groups are fluorinated lower alkoxy groups such as trifluoromethoxy, difluoromethoxy and fluoromethoxy, with trifluoromethoxy being especially preferred.

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, salicylic acid, p-toluenesulphonic acid and the like, which are non toxic to living organisms. Preferred salts with acids are formates, maleates, citrates, hydrochlorides, hydrobromides and methanesulfonic acid salts, with hydrochlorides being especially preferred.

In one embodiment, the present invention relates to a compound of formula (I), wherein $R^1$ is phenyl, or phenyl mono-, di- or tri-substituted, independently, by halogen such as chloro, by lower alkoxy such as methoxy, ethoxy, and isopropoxy, by lower alkyl such as methyl, halogenated-lower alkoxy such as trifluoromethoxy, or by di-lower alkylamino such as dimethylamino and diethylamino. In a preferable embodiment, R' is phenyl mono- or di-substituted, independently, by halogen such as chloro, or lower alkoxy such as methoxy. Most preferable R' are 4-chlorophenyl, 4-chloro-3-methoxy-phenyl and 3,4-dimethoxyphenyl.

In another embodiment, the present invention relates to a compound of formula (I), wherein $R^2$ is phenyl, or phenyl mono-, di- or tri-substituted, independently, by halogen such as chloro and fluoro, by halogenated-lower alkyl such as trifluoromethyl, by nitro or by cyano. In a preferable embodiment, $R^2$ is phenyl mono-substituted with halogen. Most preferable $R^2$ is ortho-chloro-phenyl or 2,4-dichlorophenyl.

In another embodiment, the present invention relates to a compound of formula (I), wherein $R^3$ is hydrogen, lower alkyl, benzyl, lower alkoxy, halogen, cyano, nitro, amino, —NHSO$_2$—$R^{3a}$ or —NHCO—$R^{3b}$. In a preferable embodiment, $R^3$ is hydrogen, nitro, amino, —NHSO$_2$—$R^{3a}$ or —NHCO—$R^{3b}$. Most preferable $R^3$ is hydrogen.

Substituent $R^3$ can be present at positions 4, 5, 6 or 7 of the benzthiazole ring. Preferably, substituent $R^3$ is at the 6-position of the benzthiazole ring.

In another embodiment, the present invention relates to a compound of formula (I) for use as therapeutically active substance as defined above, wherein $R^{3a}$ is lower alkyl such as methyl or n-butyl, di-lower alkylamino such as dimethylamino, benzyl, phenyl or phenyl mono-, di- or tri-substituted, independently, by lower alkyl such as methyl.

In another embodiment, the present invention relates to a compound of formula (I) for use as therapeutically active substance as defined above, wherein $R^{3b}$ is lower alkyl, di-lower alkylamino, benzyl, phenyl or phenyl mono-, di- or tri-substituted, independently, by lower alkyl such as methyl. In a preferable embodiment, $R^{3b}$ is benzyl or phenyl mono-substituted by lower alkyl, such as methyl.

In another embodiment, the present invention relates to compounds of formula (Ia)

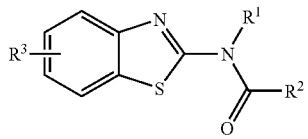

or pharmaceutically acceptable salts thereof, wherein
$R^1$ is phenyl, or phenyl mono-, di- or tri-substituted, independently, by halogen, lower alkoxy, lower alkyl, halogenated-lower alkoxy or di-lower alkylamino;
$R^2$ is phenyl, or phenyl mono-, di- or tri-substituted, independently, by halogen, halogenated-lower alkyl, nitro or cyano;
$R^3$ is hydrogen, lower alkyl, benzyl, lower alkoxy, cyano, nitro, amino, —NHSO$_2$—$R^{3a}$ or —NHCO—$R^{3b}$;
$R^{3a}$ is lower alkyl, di-lower alkylamino, benzyl, phenyl or phenyl mono-, di- or tri-substituted, independently, by lower alkyl;
$R^{3b}$ is benzyl, phenyl or phenyl mono-, di- or tri-substituted, independently, by lower alkyl;
provided that when $R^3$ is hydrogen, $R^1$ is selected from the group consisting of 2-halogen-phenyl, 4-lower alkoxy-phenyl, 3-lower alkyl-phenyl, 4-halogen-2-lower alkyl-phenyl, 3-halogen-2-lower alkyl-phenyl, 4-halogen-3-lower alkyl-phenyl, 2-halogen-4-lower alkyl-phenyl, 3-halogen-4-lower alkyl-phenyl, 2-lower alkoxy-4-lower alkyl-phenyl, 3-lower alkoxy-4-lower alkyl-phenyl, 4-lower alkoxy-2-lower alkyl-phenyl, 4-lower alkoxy-3-lower alkyl-phenyl, 3-lower alkoxy-2-lower alkyl-phenyl,
phenyl substituted by halogenated-lower alkoxy or di-lower alkylamino,
phenyl substituted by two or three groups independently selected from halogen, lower alkoxy, halogenated alkoxy and di-lower alkylamino,
phenyl substituted by a lower alkyl group and one or two groups selected from halogenated alkoxy and di-lower alkylamino, and
phenyl substituted by two lower alkyl groups and a group selected from halogen, lower alkoxy, halogenated alkoxy and di-lower alkylamino.

In a preferred embodiment, the invention relates to compounds of formula (Ia) or pharmaceutically acceptable salts thereof, wherein
$R^1$ is phenyl, or phenyl mono-, di- or tri-substituted, independently, by halogen, lower alkoxy, lower alkyl, halogenated-lower alkoxy or di-lower alkylamino;
$R^2$ is phenyl, or phenyl mono-, di- or tri-substituted, independently, by halogen, halogenated-lower alkyl, nitro or cyano;
$R^3$ is lower alkyl, benzyl, lower alkoxy, cyano, nitro, amino, —NHSO$_2$—$R^{3a}$ or —NHCO—$R^{3b}$;
$R^{3a}$ is lower alkyl, di-lower alkylamino, benzyl, phenyl or phenyl mono-, di- or tri-substituted, independently, by lower alkyl; and
$R^{3b}$ is benzyl, phenyl or phenyl mono-, di- or tri-substituted, independently, by lower alkyl.

The following compounds of formula (Ia) are examples thereof:
2-chloro-N-(4-ethoxy-phenyl)-4-fluoro-N-(6-nitro-benzothiazol-2-yl)-benzamide,
2-chloro-N-(4-ethoxy-phenyl)-N-(6-nitro-benzothiazol-2-yl)-benzamide,
2,4-dichloro-N-(4-ethoxy-phenyl)-N-(6-nitro-benzothiazol-2-yl)-benzamide,
2,4-dichloro-N-(3,4-dimethoxy-phenyl)-N-(6-nitro-benzothiazol-2-yl)-benzamide,
N-(6-amino-benzothiazol-2-yl)-2,4-dichloro-N-(3,4-dimethoxy-phenyl)-benzamide,
2,4-dichloro-N-(3,4-dimethoxy-phenyl)-N-(6-methanesulfonylamino-benzothiazol-2-yl)-benzamide,
N-[6-(butane-1-sulfonylamino)-benzothiazol-2-yl]-2,4-dichloro-N-(3,4-dimethoxy-phenyl)-benzamide,
N-[6-(dimethylamino-1-sulfonylamino)-benzothiazol-2-yl]-2,4-dichloro-N-(3,4-dimethoxy-phenyl)-benzamide,
N-(6-benzenesulfonylamino-benzothiazol-2-yl)-2,4-dichloro-N-(3,4-dimethoxy-phenyl)-benzamide,
2,4-dichloro-N-(3,4-dimethoxy-phenyl)-N-(6-phenyl-methanesulfonylamino-benzothiazol-2-yl)-benzamide,
2,4-dichloro-N-(3,4-dimethoxy-phenyl)-N-[6-(toluene-2-sulfonylamino)-benzothiazol-2-yl]-benzamide,
2,4-dichloro-N-(3,4-dimethoxy-phenyl)-N-(6-phenylacetylamino-benzothiazol-2-yl)-benzamide,
2-chloro-N-(3,4-dimethoxy-phenyl)-N-(6-nitro-benzothiazol-2-yl)-beniamide,
N-(6-amino-benzothiazol-2-yl)-2-chloro-N-(3,4-dimethoxy-phenyl)-benzamide,
2-chloro-N-(3,4-dimethoxy-phenyl)-N-(6-methanesulfonylamino-benzothiazol-2-yl)-benzamide
N-[6-(butane-1-sulfonylamino)-benzothiazol-2-yl]-2-chloro-N-(3,4-dimethoxy-phenyl)-benzamide
N-[6-(dimethylamino-1-sulfonylamino)-benzothiazol-2-yl]-2-chloro-N-(3,4-dimethoxy-phenyl)-benzamide
N-(6-benzenesulfonylamino-benzothiazol-2-yl)-2-chloro-N-(3,4-dimethoxy-phenyl)-benzamide
2-chloro-N-(3,4-dimethoxy-phenyl)-N-(6-phenylmethanesulfonylamino-benzothiazol-2-yl)-benzamide
2-chloro-N-(3,4-dimethoxy-phenyl)-N-[6-(toluene-2-sulfonylamino) benzothiazol-2-yl]-benzamide,
N-(6-(2-methylbenzoylamino)-benzothiazol-2-yl)-2-chloro-N-(3,4-dimethoxy-phenyl)-benzamide,
or pharmaceutically acceptable salts thereof.

In a further preferred embodiment, the invention relates to compounds of formula (Ia) as defined above, wherein $R^3$ is hydrogen and $R^1$ is selected from 3,5-dichlorophenyl, 3,4-dichlorophenyl, 4-chloro-2-methyl-phenyl and 4-chloro-3-methoxyphenyl.

In another preferred embodiment, the invention relates to compounds of formula (Ia) as defined above, wherein $R^3$ is hydrogen and $R^1$ is selected from 4-lower alkoxy-phenyl, 3,4-di-lower alkoxy-phenyl, 3,4,5-tri-lower alkoxy-phenyl and 3-lower alkoxy-4-lower alkyl-phenyl.

In another preferred embodiment, the invention relates to compounds of formula (Ia) as defined above, wherein $R^3$ is hydrogen and $R^1$ is phenyl substituted by halogenated-lower alkoxy or di-lower alkylamino.

Preferred compounds of formula (Ia) wherein $R^3$ is hydrogen are the following:
N-benzothiazol-2-yl-2-chloro-N-(3,5-dichloro-phenyl)-benzamide,
N-benzothiazol-2-yl-2-chloro-N-(3,4-dichloro-phenyl)-benzamide,
N-benzothiazol-2-yl-2,4-dichloro-N-(3,4-dichloro-phenyl)-benzamide,
N-benzothiazol-2-yl-2-chloro-N-(4-methoxy-phenyl)-benzamide,
N-benzothiazol-2-yl-2,4-dichloro-N-(4-methoxy-phenyl)-benzamide, N-benzothiazol-2-yl-2,4-dichloro-N-(4-chloro-2-methyl-phenyl)-benzamide,
N-benzothiazol-2-yl-2-fluoro-N-(4-methoxy-phenyl)-4-trifluoromethyl-benzamide,
N-benzothiazol-2-yl-N-(4-methoxy-phenyl)-2,4-bis-trifluoromethyl-benzamide,
N-benzothiazol-2-yl-2-chloro-4-fluoro-N-(4-methoxy-phenyl)-benzamide,
N-benzothiazol-2-yl-2-chloro-N-(4-methoxy-phenyl)-4-nitro-benzamide,
N-benzothiazol-2-yl-4-cyano-N-(4-methoxy-phenyl)-benzamide,
N-benzothiazol-2-yl-N-(4-ethoxy-phenyl)-2-fluoro-4-trifluoromethyl-benzamide,
N-benzothiazol-2-yl-2-chloro-N-(4-ethoxy-phenyl)-4-fluoro-benzamide,
N-benzothiazol-2-yl-2-chloro-N-(4-ethoxy-phenyl)-4-nitro-benzamide,
N-benzothiazol-2-yl-4-cyano-N-(4-ethoxy-phenyl)-benzamide,
N-benzothiazol-2-yl-2-chloro-N-(4-ethoxy-phenyl)-benzamide,
N-benzothiazol-2-yl-2,4-dichloro-N-(4-ethoxy-phenyl)-benzamide,
N-benzothiazol-2-yl-N-(3,4-dimethoxy-phenyl)-2-fluoro-4-trifluoromethyl-benzamide,
N-benzothiazol-2-yl-N-(3,4-dimethoxy-phenyl)-2,4-bis-trifluoromethyl-benzamide,
N-benzothiazol-2-yl-2-chloro-N-(3,4-dimethoxy-phenyl)-4-fluoro-benzamide,
N-benzothiazol-2-yl-2-chloro-N-(3,4-dimethoxy-phenyl)-4-nitro-benzamide,
N-benzothiazol-2-yl-2-chloro-N-(3,4-dimethoxy-phenyl)-benzamide,
N-benzothiazol-2-yl-2,4-dichloro-N-(3,4-dimethoxy-phenyl)-benzamide,
N-benzothiazol-2-yl-2-chloro-N-(4-dimethylamino-phenyl)-4-fluoro-benzamide,
N-benzothiazol-2-yl-2-chloro-N-(4-dimethylamino-phenyl)-benzamide,
N-benzothiazol-2-yl-2-chloro-N-(4-diethylamino-phenyl)-4-nitro-benzamide,
N-benzothiazol-2-yl-2,4-dichloro-N-(4-diethylamino-phenyl)-benzamide,
N-benzothiazol-2-yl-2-chloro-N-(3-methoxy-4-methyl-phenyl)-benzamide,
N-benzothiazol-2-yl-2-chloro-N-(3,4-diethoxy-phenyl)-benzamide,
N-benzothiazol-2-yl-2-chloro-N-(3,4,5-trimethoxy-phenyl)-benzamide,
N-benzothiazol-2-yl-2,4-dichloro-N-(3,4-diethoxy-phenyl)-benzamide,
N-benzothiazol-2-yl-2,4-dichloro-N-(3,4,5-trimethoxy-phenyl)-benzamide,
N-benzothiazol-2-yl-2-chloro-4-fluoro-N-(3-methoxy-4-methyl-phenyl)-benzamide,
N-benzothiazol-2-yl-2-chloro-N-(3,4-diethoxy-phenyl)-4-fluoro-benzamide,
N-benzothiazol-2-yl-2-chloro-4-fluoro-N-(4-isopropoxy-phenyl)-benzamide,
N-benzothiazol-2-yl-2-chloro-4-fluoro-N-(3,4,5-trimethoxy-phenyl)-benzamide,
N-benzothiazol-2-yl-2-chloro-N-(4-trifluoromethoxy-phenyl)-benzamide,
N-benzothiazol-2-yl-2,4-dichloro-N-(4-trifluoromethoxy-phenyl)-benzamide,
N-benzothiazol-2-yl-2-chloro-4-fluoro-N-(4-trifluoromethoxy-phenyl)-benzamide,
N-benzothiazol-2-yl-2-chloro-N-(4-chloro-3-methoxy-phenyl)-benzamide,
N-benzothiazol-2-yl-2,4-dichloro-N-(4-chloro-3-methoxy-phenyl)-benzamide,
N-benzothiazol-2-yl-2-chloro-4-fluoro-N-(4-chloro-3-methoxy-phenyl)-benzamide,
and pharmaceutically acceptable salts thereof.

Preferred compounds of general formula (I) are the compounds selected from the group consisting of:
N-benzothiazol-2-yl-2-chloro-N-(4-chloro-phenyl)-benzamide,
N-benzothiazol-2-yl-2-chloro-N-(3,5-dichloro-phenyl)-benzamide,
N-benzothiazol-2-yl-2-chloro-N-(3,4-dichloro-phenyl)-benzamide,
N-benzothiazol-2-yl-2,4-dichloro-N-(3,4-dichloro-phenyl)-benzamide,
N-benzothiazol-2-yl-2-chloro-N-(4-methoxy-phenyl)-benzamide,
N-benzothiazol-2-yl-2,4-dichloro-N-(4-methoxy-phenyl)-benzamide,
N-benzothiazol-2-yl-2,4-dichloro-N-(4-chloro-2-methyl-phenyl)-benzamide,
N-benzothiazol-2-yl-2-fluoro-N-(4-methoxy-phenyl)-4-trifluoromethyl-benzamide,
N-benzothiazol-2-yl-N-(4-methoxy-phenyl)-2,4-bis-trifluoromethyl-benzamide,
N-benzothiazol-2-yl-2-chloro-4-fluoro-N-(4-methoxy-phenyl)-benzamide,
N-benzothiazol-2-yl-2-chloro-N-(4-methoxy-phenyl)-4-nitro-benzamide,
N-benzothiazol-2-yl-4-cyano-N-(4-methoxy-phenyl)-benzamide,
N-benzothiazol-2-yl-N-(4-ethoxy-phenyl)-2-fluoro-4-trifluoromethyl-benzamide,
N-benzothiazol-2-yl-2-chloro-N-(4-ethoxy-phenyl)-4-fluoro-benzamide,
N-benzothiazol-2-yl-2-chloro-N-(4-ethoxy-phenyl)-4-nitro-benzamide,
N-benzothiazol-2-yl-4-cyano-N-(4-ethoxy-phenyl)-benzamide,
N-benzothiazol-2-yl-2-chloro-N-(4-ethoxy-phenyl)-benzamide,
N-benzothiazol-2-yl-2,4-dichloro-N-(4-ethoxy-phenyl)-benzamide,
N-benzothiazol-2-yl-N-(3,4-dimethoxy-phenyl)-2-fluoro-4-trifluoromethyl-benzamide,
N-benzothiazol-2-yl-N-(3,4-dimethoxy-phenyl)-2,4-bis-trifluoromethyl-benzamide,
N-benzothiazol-2-yl-2-chloro-N-(3,4-dimethoxy-phenyl)-4-fluoro-benzamide,
N-benzothiazol-2-yl-2-chloro-N-(3,4-dimethoxy-phenyl)-4-nitro-benzamide, N-benzothiazol-2-yl-2-chloro-N-(3,4-dimethoxy-phenyl)-benzamide,
N-benzothiazol-2-yl-2,4-dichloro-N-(3,4-dimethoxy-phenyl)-benzamide,
N-benzothiazol-2-yl-2-chloro-N-(4-dimethylamino-phenyl)-4-fluoro-benzamide,
N-benzothiazol-2-yl-2-chloro-N-(4-dimethylamino-phenyl)-benzamide,
N-benzothiazol-2-yl-2-chloro-N-(4-diethylamino-phenyl)-4-nitro-benzamide,
N-benzothiazol-2-yl-2,4-dichloro-N-(4-diethylamino-phenyl)-benzamide,
2-chloro-N-(4-ethoxy-phenyl)-4-fluoro-N-(6-nitro-benzothiazol-2-yl)-benzamide,
2-chloro-N-(4-ethoxy-phenyl)-N-(6-nitro-benzothiazol-2-yl)-benzamide,
2,4-dichloro-N-(4-ethoxy-phenyl)-N-(6-nitro-benzothiazol-2-yl)-benzamide,
N-benzothiazol-2-yl-2-chloro-N-(3-methoxy-phenyl)-benzamide,
N-benzothiazol-2-yl-2,4-dichloro-N-(3-methoxy-phenyl)-benzamide,
N-benzothiazol-2-yl-2-chloro-N-(3-methoxy-4-methyl-phenyl)-benzamide,
N-benzothiazol-2-yl-2-chloro-N-(3,4-diethoxy-phenyl)-benzamide,
N-benzothiazol-2-yl-2-chloro-N-(3,4,5-trimethoxy-phenyl)-benzamide,
N-benzothiazol-2-yl-2,4-dichloro-N-(3,4-diethoxy-phenyl)-benzamide,
N-benzothiazol-2-yl-2,4-dichloro-N-(3,4,5-trimethoxy-phenyl)-benzamide,
N-benzothiazol-2-yl-2-chloro-4-fluoro-N-(3-methoxy-4-methyl-phenyl)-benzamide,
N-benzothiazol-2-yl-2-chloro-N-(3,4-diethoxy-phenyl)-4-fluoro-benzamide,
N-benzothiazol-2-yl-2-chloro-4-fluoro-N-(4-isopropoxy-phenyl)-benzamide,
N-benzothiazol-2-yl-2-chloro-4-fluoro-N-(3,4,5-trimethoxy-phenyl)-benzamide,
2,4-dichloro-N-(3,4-dimethoxy-phenyl)-N-(6-nitro-benzothiazol-2-yl)-benzamide,
N-(6-amino-benzothiazol-2-yl)-2,4-dichloro-N-(3,4-dimethoxy-phenyl)-benzamide,
2,4-dichloro-N-(3,4-dimethoxy-phenyl)-N-(6-methanesulfonylamino-benzothiazol-2-yl)-benzamide,
N-[6-(butane-1-sulfonylamino)-benzothiazol-2-yl]-2,4-dichloro-N-(3,4-dimethoxy-phenyl)-benzamide,
N-[6-(dimethylamino-1-sulfonylamino)-benzothiazol-2-yl]-2,4-dichloro-N-(3,4-dimethoxy-phenyl)-benzamide,
N-(6-benzenesulfonylamino-benzothiazol-2-yl)-2,4-dichloro-N-(3,4-dimethoxy-phenyl)-benzamide,
2,4-dichloro-N-(3,4-dimethoxy-phenyl)-N-(6-phenylmethanesulfonylamino-benzothiazol-2-yl)-benzamide,
2,4-dichloro-N-(3,4-dimethoxy-phenyl)-N-[6-(toluene-2-sulfonylamino)-benzothiazol-2-yl]-benzamide,
2,4-dichloro-N-(3,4-dimethoxy-phenyl)-N-(6-phenylacetylamino-benzothiazol-2-yl)-benzamide,
2-chloro-N-(3,4-dimethoxy-phenyl)-N-(6-nitro-benzothiazol-2-yl)-benzamide,
N-(6-amino-benzothiazol-2-yl)-2-chloro-N-(3,4-dimethoxy-phenyl)-benzamide,
2-chloro-N-(3,4-dimethoxy-phenyl)-N-(6-methanesulfonylamino-benzothiazol-2-yl)-benzamide,
N-[6-(butane-1-sulfonylamino)-benzothiazol-2-yl]-2-chloro-N-(3,4-dimethoxy-phenyl)-benzamide,
N-[6-(dimethylamino-1-sulfonylamino)-benzothiazol-2-yl]-2-chloro-N-(3,4-dimethoxy-phenyl)-benzamide,
N-(6-benzenesulfonylamino-benzothiazol-2-yl)-2-chloro-N-(3,4-dimethoxy-phenyl)-benzamide,
2-chloro-N-(3,4-dimethoxy-phenyl)-N-(6-phenylmethanesulfonylamino-benzothiazol-2-yl)-benzamide,
2-chloro-N-(3,4-dimethoxy-phenyl)-N-[6-(toluene-2-sulfonylamino)-benzothiazol-2-yl]-benzamide,
N-(6-(2-methylbenzoylamino)-benzothiazol-2-yl)-2-chloro-N-(3,4-dimethoxy-phenyl)-benzamide,
N-benzothiazol-2-yl-2-chloro-N-(4-trifluoromethoxy-phenyl)-benzamide,
N-benzothiazol-2-yl-2,4-dichloro-N-(4-trifluoromethoxy-phenyl)-benzamide,
N-benzothiazol-2-yl-2-chloro-4-fluoro-N-(4-trifluoromethoxy-phenyl)-benzamide,
N-benzothiazol-2-yl-2-chloro-N-(4-chloro-3-methoxy-phenyl)-benzamide,
N-benzothiazol-2-yl-2,4-dichloro-N-(4-chloro-3-methoxy-phenyl)-benzamide,
N-benzothiazol-2-yl-2-chloro-4-fluoro-N-(4-chloro-3-methoxy-phenyl)-benzamide,
and pharmaceutically acceptable salts thereof.

Most preferred compounds of general formula (I) are those selected from the group consisting of:
N-benzothiazol-2-yl-2,4-dichloro-N-(3,4-dichloro-phenyl)-benzamide,
N-benzothiazol-2-yl-2-chloro-N-(3,4-dimethoxy-phenyl)-4-fluoro-benzamide,
N-benzothiazol-2-yl-2-chloro-N-(3,4-dimethoxy-phenyl)-4-nitro-benzamide,
N-benzothiazol-2-yl-2-chloro-N-(3,4-dimethoxy-phenyl)-benzamide,
N-benzothiazol-2-yl-2,4-dichloro-N-(3,4-dimethoxy-phenyl)-benzamide,
2,4-dichloro-N-(4-ethoxy-phenyl)-N-(6-nitro-benzothiazol-2-yl)-benzamide,
N-benzothiazol-2-yl-2-chloro-N-(3-methoxy-phenyl)-benzamide,
N-benzothiazol-2-yl-2,4-dichloro-N-(3-methoxy-phenyl)-benzamide,
N-benzothiazol-2-yl-2,4-dichloro-N-(3,4-diethoxy-phenyl)-benzamide,
N-[6-(butane-1-sulfonylamino)-benzothiazol-2-yl]-2,4-dichloro-N-(3,4-dimethoxy-phenyl)-benzamide,
N-benzothiazol-2-yl-2-chloro-N-(4-chloro-3-methoxy-phenyl)-benzamide,
N-benzothiazol-2-yl-2,4-dichloro-N-(4-chloro-3-methoxy-phenyl)-benzamide,
and pharmaceutically acceptable salts thereof.

The compounds of formula (I) may be prepared using the general methods described below:

The preparation of compounds of formula (I) or formula (Ia) of the present invention (compounds of formulae IB, IC and ID, respectively, in Scheme 1 below) may be carried out in sequential or convergent synthetic routes. Syntheses of the compounds of the present invention are illustrated in the following Scheme 1. The skills required for carrying out the reaction and purification of the resulting products are known to those in the art. The substituents and indices used in the following description of the processes have the significance given above unless indicated to the contrary.

Scheme 1:

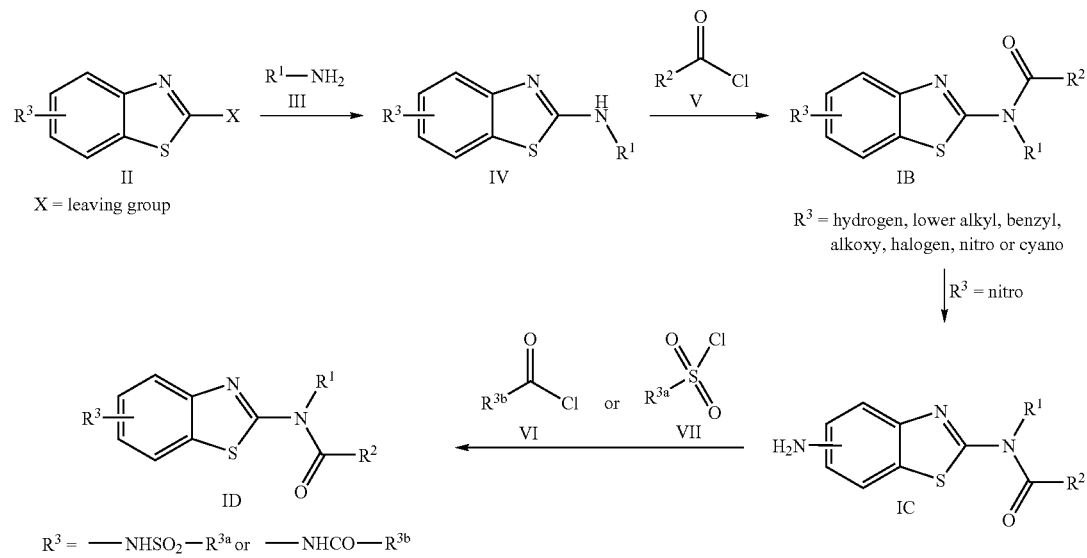

Compounds of formula IB (compounds of formula I wherein $R^3$ is hydrogen, lower alkyl, benzyl, alkoxy, halogen, nitro or cyano) can be prepared according to Scheme 1 as follows:

(a) N-aryl-1,3-benzothiazole-2-amine derivatives IV are either commercially available or can be prepared from commercially available precursors by methods known in the art, preferably from a suitable 1,3-benzothiazole II, which are either commercially available or synthetically accessible via general procedures described for example in EP 0 043 013 (X=suitable leaving group which does not cause adverse side reaction during the preparation procedure; commonly Cl or halogen, and the like), and an aniline III (commercially available) by mixing the starting materials with or without a solvent in the presence or absence of an acid. There is no particular restriction on the nature of the solvent to be employed, provided that it has no adverse effect on the reaction or the reagents involved and that it can dissolve the reagents, at least to some extent. Examples for suitable solvents include: ethanol, methanol, dioxane, and the like. There is no particular restriction on the nature of the acid used in this stage, and any acid commonly used in this type of reaction may equally be employed here. Examples of such acids include: HCl, HOAc, and the like in a solvent or without a solvent present. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the respective N-aryl-1,3-benzothiazole-2-amine derivatives IV. This described conversion can be effected by methods described in literature (see for example WO97/49704 or Sawhney, S. N.; Akora, S. K.; Singh, J. V.; Bansal, O. P.; Singh, S. P., Indian J. Chem. 1978, 16, 605-609).

(b) The conversion of the respective N-aryl-1,3-benzothiazole-2-amine derivatives IV to access the corresponding 1,3-benzothiazol-2-yl-N-aryl-benzamide derivatives IB can be carried out from suitable starting materials according to methods known in the art. For example, the conversion of the aniline-moiety of compounds of formula IV can be effected by reaction of IV with suitable acid chlorides V in the presence or absence of a solvent and in the presence or the absence of a base to obtain the respective amides IB. There is no particular restriction on the nature of the solvent to be employed, provided that it has no adverse effect on the reaction or the reagents involved and that it can dissolve the reagents, at least to some extent. Examples for suitable solvents include: dichloromethane, THF, dioxane, and the like. There is no particular restriction on the nature of the base used in this stage, and any base commonly used in this type of reaction may equally be employed here. Examples of such bases include triethylamine, diisopropylethylamine, potassium tert-butoxide (KOtBu), and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the desired 1,3-benzothiazol-2-yl-N-aryl-benzamide derivatives IA. This type of conversion can be effected by methods described in literature (see, for example, Comprehensive Organic Transformations: A Guide to Functional Group Preparations, 2nd Edition, Richard C. Larock. John Wiley & Sons, New York, N.Y. 1999). The resulting compounds of formula IB (compounds of formula I wherein $R^3$ is hydrogen, lower alkyl, benzyl, alkoxy, halogen, nitro or cyano) are compounds of the present invention and may be the desired product; alternatively they may be subjected to consecutive reactions.

Compounds of formula IC (compounds of formula I wherein $R^3$ is amino) can be prepared according to Scheme 1 as follows:

(a) Compounds of formula IB wherein $R^3$ is nitro can be converted to their respective amine-derivatives IC by reduction methods which are widely described in literature and known to those skilled in the art. For example, the reduction of the nitro-functionality of compounds of formula IB ($R^3$=nitro; preferably in position 6) can be effected by reaction of IB ($R^3$=nitro; preferably in position 6) with a reducing agent in the presence or absence of a solvent and in the presence or absence of an acid. There is no particular restriction on the nature of the reducing agent used in this stage, and any reducing agent commonly used in this type of reaction may equally be employed here. Examples of such reducing agents include tinchloride, hydrogen, and the like. There is no particular restriction on the nature of the acid used in this stage, and any acid commonly used in this type of reaction may equally be employed here. Examples of such acids include HCl, HOAc, and the like in a solvent or without a solvent present. There is no particular restriction on the nature of the solvent to be employed, provided that it has no adverse effect on the reaction or the reagents involved and that it can dissolve the reagents, at least to some extent. Examples for suitable solvents include dimethylformamide (DMF), tetrahydrofuran (THF), dioxane, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the desired products ID. The resulting compounds of formula ID are compounds of the present invention and may be the desired product; alternatively they may be subjected to consecutive reactions.

Compounds of formula ID (compounds of formula I wherein $R^3$ is —$NHSO_2$—$R^{3a}$, or —NHCO—$R^{3b}$) can be prepared according to Scheme 1 as follows:

Compounds of formula ID can be prepared from suitable starting materials according to methods known in the art. The conversion of the amino-moiety in IC to access sulfonamides or amides ID ($R^3$=—$NHSO_2$—$R^{3a}$ or —NHCO—$R^{3b}$; preferably in position 6) can be effected by methods described in literature. For example the conversion of the amine derivatives IC or their respective salts to access compounds of formula ID is effected by reaction of IC with suitable acid chlorides VI or sulfonyl chlorides VII (compounds known or compounds prepared by known methods) respectively in the presence or absence of a solvent and in the presence or the absence of a base. There is no particular restriction on the nature of the solvent to be employed, provided that it has no adverse effect on the reaction or the reagents involved and that it can dissolve the reagents, at least to some extent. Examples for suitable solvents include dichloromethane (DCM), dioxane, tetrahydrofuran (THF), and the like. There is no particular restriction on the nature of the base used in this stage, and any base commonly used in this type of reaction may equally be employed here. Examples of such bases include triethylamine, diisopropylethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield amide or sulfonamide derivatives ID ($R^3$=—$NHSO_2$—$R^{3a}$ or —NHCO—$R^{3b}$; preferably in position 6). For reaction conditions described in literature effecting such reactions see for example Comprehensive Organic Transformations: A Guide to Functional Group Preparations, 2nd Edition, Richard C. Larock. John Wiley & Sons, New York, N.Y. 1999.

It will be appreciated, that the compounds of general formula (I) in this invention may be derivatised at functional groups to provide derivatives which are capable of conversion back to the parent compound in vivo.

As described above, the compounds of formula (I) or pharmaceutically acceptable salts thereof can be used as therapeutically active substances, especially as therapeutically active substances for the treatment and/or prophylaxis of diseases which are associated with the modulation of the CB1 receptors. In one embodiment, the invention therefore relates to compounds as defined above for use as therapeutic active substances, particularly as therapeutic active substances for the treatment and/or prophylaxis of diseases which are associated with the modulation of CB1 receptors.

The invention also relates to pharmaceutical compositions comprising a compound of formula (I):

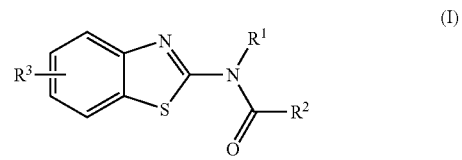

(I)

wherein $R^1$ is phenyl, or phenyl mono-, di- or tri-substituted, independently, by halogen, lower alkoxy, lower alkyl, halogenated-lower alkoxy or di-lower alkylamino;

$R^2$ is phenyl, or phenyl mono-, di- or tri-substituted, independently, by halogen, halogenated-lower alkyl, nitro or cyano;

$R^3$ is hydrogen, lower alkyl, benzyl, lower alkoxy, halogen, cyano, nitro, amino, —$NHSO_2$—$R^{3a}$ or —NHCO—$R^{3b}$;

$R^{3a}$ is lower alkyl, di-lower alkylamino, benzyl, phenyl or phenyl mono-, di- or tri-substituted, independently, by lower alkyl;

$R^{3b}$ is benzyl, phenyl or phenyl mono-, di- or tri-substituted, independently, by lower alkyl;

or a pharmaceutically acceptable salt thereof, and a pharmaceutically acceptable carrier and/or adjuvant.

In another embodiment, the invention relates to a method for the treatment and/or prophylaxis of diseases which are associated with the modulation of CB1 receptors, which method comprises administering a compound of formula (I):

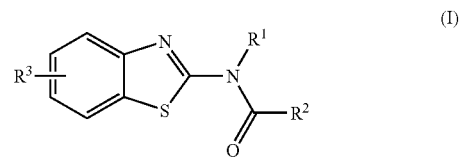

(I)

wherein $R^1$ is phenyl, or phenyl mono-, di- or tri-substituted, independently, by halogen, lower alkoxy, lower alkyl, halogenated-lower alkoxy or di-lower alkylamino;

$R^2$ is phenyl, or phenyl mono-, di- or tri-substituted, independently, by halogen, halogenated-lower alkyl, nitro or cyano;

R³ is hydrogen, lower alkyl, benzyl, lower alkoxy, halogen, cyano, nitro, amino, —NHSO₂—R³ᵃ or —NHCO—R³ᵇ;

R³ᵃ is lower alkyl, di-lower alkylamino, benzyl, phenyl or phenyl mono-, di- or tri-substituted, independently, by lower alkyl;

R³ᵇ is benzyl, phenyl or phenyl mono-, di- or tri-substituted, independently, by lower alkyl;

or a pharmaceutically acceptable salt thereof, to a human being or animal.

The invention further relates to the use of compounds as defined above for the treatment and/or prophylaxis of diseases which are associated with the modulation of CB1 receptors.

In addition, the invention relates to the use of compounds of formula (I),

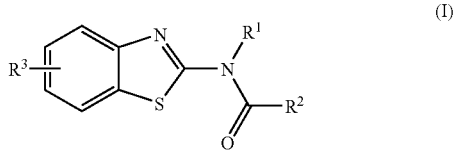

(I)

wherein

R¹ is phenyl, or phenyl mono-, di- or tri-substituted, independently, by halogen, lower alkoxy, lower alkyl, halogenated-lower alkoxy or di-lower alkylamino;

R² is phenyl, or phenyl mono-, di- or tri-substituted, independently, by halogen, halogenated-lower alkyl, nitro or cyano;

R³ is hydrogen, lower alkyl, benzyl, lower alkoxy, halogen, cyano, nitro, amino, —NHSO₂—R³ᵃ or —NHCO—R³ᵇ;

R³ᵃ is lower alkyl, di-lower alkylamino, benzyl, phenyl or phenyl mono-, di- or tri-substituted, independently, by lower alkyl;

R³ᵇ is benzyl, phenyl or phenyl mono-, di- or tri-substituted, independently, by lower alkyl;

or of a pharmaceutically acceptable salt thereof, for the preparation of medicaments for the treatment and/or prophylaxis of diseases which are associated with the modulation of CB1 receptors. Such medicaments comprise a compound as defined above.

In this context, the expression 'diseases associated with modulation of CB1 receptors' means diseases which can be treated and/or prevented by modulation of CB1 receptors. Such diseases encompass, but are not limited to, psychic disorders, especially anxiety and anxiety disorders, psychosis, schizophrenia, depression, substance abuse disorders including abuse of psychotropes, for example for the abuse and/or dependence of substances, including alcohol dependency and nicotine dependency, neuropathies, migraine, stress, epilepsy, dyskinesias, Parkinson's disease, amnesia, memory and cognitive disorders, senile dementia, Alzheimer's disease, eating disorders, obesity, diabetes type II or non insulin dependent diabetes (NIDD), gastrointestinal diseases, vomiting, diarrhea, urinary disorders, cardiovascular disorders, infertility disorders, inflammations, infections, cancer, demyelinisation related disorders, neuroinflammation, in particular in atherosclerosis, or the Guillain-Barré syndrome, viral encephalitis, cerebral vascular incidents and cranial trauma.

In a preferable aspect, the expression 'diseases associated with modulation of CB1 receptors' relates to eating disorders, obesity, diabetes type II or non insulin dependent diabetes (NIDD), neuroinflammation, diarrhea, abuse and/or dependence of a substances, including alcohol dependency and nicotine dependency. In a more preferable aspect, the said term related to eating disorders, obesity, diabetes type II or non insulin dependent diabetes (NIDD), abuse and/or dependence of a substances, including alcohol dependency and nicotine dependency, with obesity being especially preferred.

It is a further preferred object to provide a method of treatment or prevention of Type II diabetes (non-insulin dependent diabetes mellitus (NIDDM)) in a human which comprises administration of a therapeutically effective amount of a compound according to formula (I) in combination or association with a therapeutically effective amount of a lipase inhibitor, particularly, wherein the lipase inhibitor is orlistat. Also an object of the invention is the method as described above for the simultaneous, separate or sequential administration of a compound according to formula (I) and a lipase inhibitor, particularly tetrahydrolipstatin.

It is a further preferred object to provide a method for the treatment or prevention of obesity and obesity related disorders which comprises administration of a therapeutically effective amount of a compound according to formula (I) in combination or association with a therapeutically effective amount of other drugs for the treatment of obesity or eating disorders so that together they give effective relief. Suitable other drugs include but are not limited to anorectic agents, lipase inhibitors and selective serotonin reuptake inhibitors (SSRI). Combinations or associations of the above agents may be encompassing separate, sequential or simultaneous administration.

Preferable lipase inhibitor is tetrahydrolipstatin.

Suitable anorectic agents of use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine, and pharmaceutically acceptable salts thereof.

Most preferable anorectic agents are sibutramine and phentermine.

Suitable selective serotonin reuptake inhibitors of use in combination with a compound of the present invention include: fluoxetine, fluvoxamine, paroxetine and sertraline, and pharmaceutically acceptable salts thereof.

The following tests were carried out in order to determine the activity of the compounds of formula (I).

The affinity of the compounds of the invention for cannabinoid CB1 receptors was determined using membrane preparations of human embryonic kidney (HEK) cells in which the human cannabis CB1 receptor is transiently transfected using the Semliki Forest Virus system in conjunction with [3H]-CP-55,940 as radioligand. After incubation of a freshly prepared cell membrane preparation with the [3H]-ligand, with or without addition of compounds of the invention, separation of bound and free ligand was performed by filtration over glassfiber filters. Radioactivity on the filter was measured by liquid scintillation counting.

The affinity of the compounds of the invention for cannabinoid CB2 receptors was determined using membrane preparations of human embryonic kidney (HEK) cells in which the human cannabis CB2 receptor is transiently transfected using the Semliki Forest virus system in conjunction with [3H]-CP-55,940 as radioligand. After incubation of a freshly prepared cell membrane preparation with the [3H]-ligand, with or without addition of compounds of the invention, separation of bound of bound and free ligand was performed by filtration over glassfiber filters. Radioactivity on the filter was measured by liquid scintillation counting.

The cannabinoid CB1 antagonistic activity of compounds of the invention was determined by functional studies using CHO cells in which human cannabinoid CB1 receptors are stably expressed (see M. Rinaldi-Carmona et. al., J. Pharmacol. Exp. Ther. 278 (1996) 871). The stable expression of the human cannabinoid receptor in cell systems was first described in Nature 1990, 346, 561-564 (CB1) and Nature 1993, 365, 61-65 (CB2) respectively. Adenylyl cyclase was stimulated using forskolin and measured by quantifying the amount of accumulated cyclic AMP. Concomitant activation of CB1 receptors by CB1 receptor agonists (e.g., CP-55,940 or (R)-WIN-55212-2) can attenuate the forskolin-induced accumulation of cAMP in a concentration dependent manner. This CB1 receptor mediated response can be antagonised by CB1 receptor antagonists such as the compounds of the invention.

The compounds of formula (I) show an excellent affinity for the CB1 receptor, determined with the experimental conditions described in Devane et. al., Mol. Pharmacol. 34 (1998) 605-613. The compounds of the present invention or the pharmaceutically acceptable salts or solvates are antagonists and selective for the CB1 receptor with affinities below $IC_{50}=5$ μM, preferably below $IC_{50}=2$ μM. They exhibit at least a 10 fold selectivity againsts the CB2 receptor.

| Compound of Example | $IC_{50}$ [μM] |
|---|---|
| 8 | 0.73 |
| 9 | 1.96 |
| 12 | 2.48 |
| 28 | 1.38 |
| 45 | 0.83 |
| 52 | 1.59 |
| 57 | 1.42 |

The compounds of formula (I) and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragees, hard and soft gelatine capsules, solutions, emulsions or suspensions, rectally, e.g. in the form of suppositories, parenteraily, e.g. in the form of injection solutions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula (I) and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula (I).

The following examples serve to illustrate the present invention in more detail. They are, however, not intended to limit its scope in any manner.

EXAMPLES

MS=mass spectrometry, ISP=ion spray (positive ion), corresponds to ESI (electrospray, positive ion); mp=melting point, aq=aqueous, THF=tetrahydrofuran, DMSO=dimethylsulfoxide, DMF=dimethylformamide, DCM=dichloromethane, KOtBu=potassium tert-butoxide, NMR=nuclear magnetic resonance spectroscopy.

Example 1

Starting Materials (a) Benzothiazol-2-yl-(4-chloro-phenyl)-amine

A mixture of 1.7 g (10 mmol) 2-chloro-1,3-benzothiazole and 2.6 g (10 mmol) 4-chloroaniline in 20 ml acetic acid was heated to 110° C. for 3 h. The reaction mixtures was diluted with 200 ml water and the resulting mixture was extracted with 3×150 ml ethyl acetate. The combined organic phases were washed with 2×100 ml water, dried with $MgSO_4$, filtered and evaporated to dryness. The residue was recrystallysed from a mixture of hexane/ethyl acetate to yield 1.4 g (54%) of the title compound.

1-H-NMR (300 MHz, $CDCl_3$) δ=10.6 (s, br, 1H, NH), 7.82 (m, 3H, (Ar—H-3/H-5)/H-7), 7.62 (d, J=7.8 Hz, 1H,

H-4), 7.42 (d, J=6.8 Hz, 2H, Ar—H-2/H-6), 7.35 (t, J=8.1 Hz, 1H, H-6), 7.18 (t, J=7.5 Hz, 1H, H-5). MS (m/e): 261.2 (MH+, 100%).

(b) Benzothiazol-2-yl-(3,5-dichloro-phenyl)-amine

The title compound was synthesised from 2-Chloro-benzothiazole (commercially available) and 3,5-Dichloroaniline (commercially available) according to the procedure described for, Example 1a) above.

1-H-NMR (300 MHz, CDCl$_3$) δ=7.68 (d, J=7.9 Hz, 1H, H-7), 7.63 (d, J=8.1 Hz H, H-4), 7.37 (m, 3H, H-5, (Ar—H-2/H-6)/H-6), 7.22 (t, J=7.9 Hz, 1H, H-5), 7.18 (d, J=1.7 Hz, 1H, Ar—H-4). MS (m/e): 295.2 (MH+, 100%).

(c) Benzothiazol-2-yl-(3,4-dichloro-phenyl)-amine

The title compound was synthesised from 2-Chloro-benzothiazole (commercially available) and 3,4-Dichloroaniline (commercially available) according to the procedure described for Example 1a) above.

1-H-NMR (300 MHz, DMSO-d6) δ=10.81(s, br, 1H, NH), 8.24 (d, J=2.3 Hz, 1H, Ar—H-2), 7.86 (d, J=7.8 Hz, 1H, H-7), 7.63 (m, 3H, (Ar—H-5/H-6)/H-4), 7.36 (t, J=7.8 Hz, 1H, H-6), 7.21 (t, J=7.7 Hz, 1H, H-5). MS (m/e): 295.2 (MH+, 100%).

(d) Benzothiazol-2-yl-(4-methoxy-phenyl)-amine

The title compound was synthesised from 2-Chloro-benzothiazole (commercially available) and 4-Methoxyaniline (commercially available) according to the procedure described for Example 1a) above.

1-H-NMR (300 MHz, DMSO-d6) δ=11.75(s, br, 1H, NH), 7.76 (d, J=7.7 Hz, 1H, H-7), 7.68 (d, J=8.9 Hz, 2H, (Ar—H-2/Ar—H-6)), 7.55 (d, J=7.9 Hz, 1H, H-4), 7.29 (t, J=7.7 Hz, 1H, H-6), 7.09 (t, J=7.9 Hz, 1H, H-5), 6.96 (d, J=8.9 Hz, 2H, (Ar—H-3/Ar—H-5)), 3.75 (s, 3H, OCH$_3$). MS (m/e): 257.1 (MH+, 100%).

(e) Benzothiazol-2-yl-(4-chloro-2-methyl-phenyl)-amine

The title compound was synthesised from 2-Chloro-benzothiazole (commercially available) and 4-Chloro-2-methylaniline (commercially available) according to the procedure described for Example 1a) above.

1-H-NMR (300 MHz, DMSO-d6) δ=9.68(s, br, 1H, NH), 8.01 (d, J=8.5 Hz, 1H, H-7), 7.76 (d, J=7.2 Hz, 1H, Ar—H-5), 7.50 (d, J=7.8 Hz, 1H, H-4), 7.31 (m, 3H, H-2/Ar—H-6)/H-5), 7.15 (t, J=8.5 Hz, 1H, H-6), 2.29 (s, 3H, CH$_3$). MS (m/e): 275.2 (MH+, 100%).

(f) Benzothiazol-2-yl-(4-ethoxy-phenyl)-amine

The title compound was synthesised from 2-Chloro-benzothiazole (commercially available) and 4-Ethoxyaniline (commercially available) according to the procedure described for Example 1a) above.

1-H-NMR (300 MHz, DMSO-d6) δ=10.26 (s, br, 1H, NH), 7.76 (d, J=7.5 Hz, 1H, H-7), 7.68 (d, J=6.9 Hz, 2H, (Ar—H-2/Ar—H-6)), 7.55 (d, J=7.9 Hz, 1H, H-4), 7.29 (t, J=7.5 Hz, 1H, H-6), 7.09 (t, J=7.9 Hz, 1H, H-5), 6.96 (d, J=6.9 Hz, 2H, (Ar—H-3/Ar—H-5)), 4.01 (q, J=7.0 Hz, 2H, OCH$_2$), 1.32 (t, J=7.0 Hz, 3H, CH$_3$). MS (m/e): 271.1 (MH+, 100%).

(g) Benzothiazol-2-yl-(3,4-dimethoxy-phenyl)-amine

The title compound was synthesised from 2-Chloro-benzothiazole (commercially available) and 3,4-Dimethoxyaniline (commercially available) according to the procedure described for Example 1a) above.

1-H-NMR (300 MHz, DMSO-d6) δ=10.26(s, br, 1H, NH), 7.77 (d, J=7.1 Hz, 1H, H-7), 7.53 (d, J=7.6 Hz, 1H, H-4), 7,40 (s, 1H, Ar—H-2), 7.30 (m, 2H, (Ar—H-6)/H-5), 7.15 (t, J=7.1 Hz, 1H, H-6), 6.97 (d, J=8.7 Hz, 1H, Ar—H-5), 3.78 (s, 3H, OCH$_3$), 3.74 (s, 3H, OCH$_3$). MS (m/e): 287.0 (MH+, 100%).

(h) N-Benzothiazol-2-yl-N',N'-dimethyl-benzene-1,4-diamine

The title compound was synthesised from 2-Chloro-benzothiazole (commercially available) and N,N-Dimethyl-p-phenylenediamine (commercially available) according to the procedure described for Example 1a) above.

1-H-NMR (300 MHz, DMSO-d6) δ=10.08 (s, br, 1H, NH), 7.71 (d, J=7.1 Hz, 1H, H-7), 7.50 (m, 3H, (Ar—H-2/Ar—H-6)/H4), 7.27 (t, J=7.1 Hz, 1H, H-6), 7.10 (t, J=7.8 Hz, 1H, H-5), 6.78 (d, J=9.0 Hz, 2H, (Ar—H-3/Ar—H-5)), 2.86 (s, 6H, N(CH$_3$)$_2$). MS (m/e): 270.2 (MH+, 100%).

(i) N-Benzothiazol-2-yl-N',N'-diethyl-benzene-1,4-diamine

The title compound was synthesised from 2-Chloro-benzothiazole (commercially available) and N,N-Diethyl-p-phenylenediamine (commercially available) according to the procedure described for Example 1a) above. MS (m/e): 298.2 (MH+, 100%).

(j) Benzothiazol-2-yl-(3-methoxy-phenyl)-amine

The title compound is either commercially available or can be synthesised from 2-Chloro-benzothiazole (commercially available) and 3-methoxyaniline (commercially available) according to the procedure described for Example 1a) above. MS (m/e): 257.0 (MH+, 100%).

(k) Benzothiazol-2-yl-(4-chloro-3-methoxy-phenyl)-amine

The title compound was synthesised from 2-chloro-benzothiazole (commercially available) and 4-chloro-3-methoxyaniline (commercially available) according to the procedure described for Example 1a) above. MS (m/z): 291.3 (MH+, 100%).

(l) Benzothiazol-2-yl-(4-trifluoromethoxy-phenyl)-amine

The title compound was synthesised from 2-chloro-benzothiazole (commercially available) and 4-trifluoromethoxyaniline (commercially available) according to the procedure described for Example A. MS (m/z): 310.0 (MH+, 100%).

(m) (4-Ethoxy-phenyl)-(6-nitro-benzothiazol-2-yl)-amine

The title compound was synthesised from 2-Chloro-6-nitro-benzothiazole (commercially available) and 4-ethoxyaniline (commercially available) according to the procedure described for Example 1a) above.

1-H-NMR (300 MHz, DMSO-d6) δ=10.8 (s, br, 1H, NH), 8.80 (d, J=2.4 Hz, 1H, H-7) 8.16 (dd, J1=8.9 Hz, J2=2.4 Hz, 1H, H-5), 7.65 (m, 3H, (Ar—H-2/Ar—H-6)/H4) 6.97 (d, J=6.8 Hz, 2H, (Ar—H-3/Ar—H-5)), 4.02 (q, J=6.9 Hz, 2H, OCH$_2$), 1.28 (t, J=6.9 Hz, 3H, CH$_3$). MS (m/e): 316.2 (MH+, 100%).

(n) (3,4-Dimethoxy-phenyl)-(6-nitro-benzothiazol-2-yl)-amine

The title compound was synthesised from 2-Chloro-6-nitro-benzothiazole (commercially available) and 3,4-dimethoxyaniline (commercially available) according to the procedure described for Example 1a) above. MS (m/e): 332.2 (MH+, 100%).

Example 2

N-Benzothiazol-2-yl-2-chloro-N-(4-chloro-phenyl)-benzamide

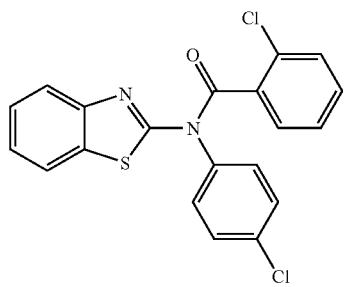

A mixture of 39.1 mg (0.15 mmol) Benzothiazol-2-yl-(4-chloro-phenyl)-amine in 0.5 ml THF, 45.2 mg (0.18 mmol) 2-chlorobenzoyl chloride in 0.18 ml THF and 0.17 ml of a 1 M solution of KOtBu in THF was heated to 50° C. for 16 h. After addition of 0.5 ml formic acid the mixtures are subjected to preparative HPLC separation on reversed phase eluting with an acetonitrile/water gradient. Evaporation of the product fractions yielded 40.1 mg (67%) of the title compound. MS (m/e): 399.3 (MH$^+$, 100%).

According to the procedure described for Example 2 N-Benzothiazol-2-yl-N-aryl-benzamide derivatives have been synthesised from Benzothiazol-2-yl-aryl-amine derivatives acid chlorides. The results are shown in table 1 below and comprise Example 3 to Example 34.

TABLE 1

| Example No. | Structure | Compound Name | Starting Materials | MW (MH$^+$, 100%) |
|---|---|---|---|---|
| 3 | 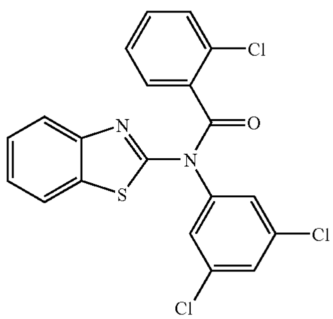 | N-Benzothiazol-2-yl-2-chloro-N-(3,5-dichloro-phenyl)-benzamide | Benzothiazol-2-yl-(3,5-dichloro-phenyl)-amine and 2-Chloro-benzoyl chloride (commercially available) | 433.2 |
| 4 | 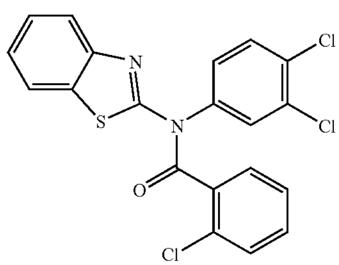 | N-Benzothiazol-2-yl-2-chloro-N-(3,4-dichloro-phenyl)-benzamide | Benzothiazol-2-yl-(3,4-dichloro-phenyl)-amine and 2-Chloro-benzoyl chloride (commercially available) | 433.0 |
| 5 | 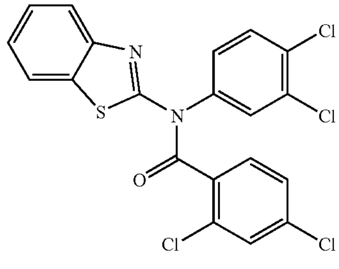 | N-Benzothiazol-2-yl-2,4-dichloro-N-(3,4-dichloro-phenyl)-benzamide | Benzothiazol-2-yl-(3,4-dichloro-phenyl)-amine and 2,4-Dichloro-benzoyl chloride (commercially available) | 469.0 |

TABLE 1-continued

| Example No. | Structure | Compound Name | Starting Materials | MW (MH+, 100%) |
|---|---|---|---|---|
| 6 | 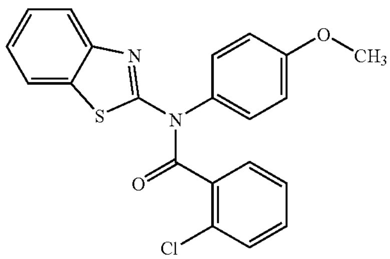 | N-Benzothiazol-2-yl-2-chloro-N-(4-methoxy-phenyl)-benzamide | Benzothiazol-2-yl-(4-methoxy-phenyl)-amine and 2-Chloro-benzoyl chloride (commercially available) | 395.3 |
| 7 | 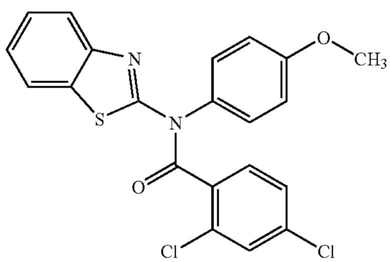 | N-Benzothiazol-2-yl-2,4-dichloro-N-(4-methoxy-phenyl)-benzamide | Benzothiazol-2-yl-(4-methoxy-phenyl)-amine and 2,4-Dichloro-benzoyl chloride (commercially available) | 429.4 |
| 8 | 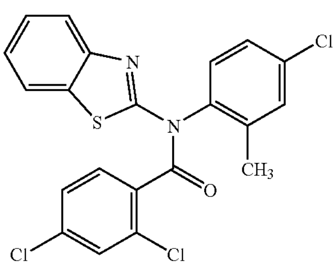 | N-Benzothiazol-2-yl-2,4-dichloro-N-(4-chloro-2-methyl-phenyl)-benzamide | Benzothiazol-2-yl-(4-chloro-2-methyl-phenyl)-amine and 2,4-Dichloro-benzoyl chloride (commercially available) | 447.1 |
| 9 | 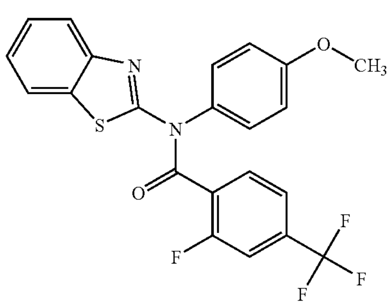 | N-Benzothiazol-2-yl-2-fluoro-N-(4-methoxy-phenyl)-4-trifluoromethyl-benzamide | Benzothiazol-2-yl-(4-methoxy-phenyl)-amine and 2-Fluoro-4-trifluoromethyl-benzoyl chloride (commercially available) | 447.2 |
| 10 | 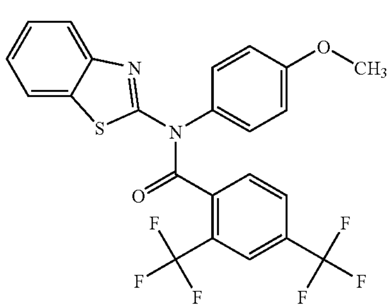 | N-Benzothiazol-2-yl-N-(4-methoxy-phenyl)-2,4-bis-trifluoromethyl-benzamide | Benzothiazol-2-yl-(4-methoxy-phenyl)-amine and 2,4-Bis-trifluoromethyl-benzoyl chloride (commercially available) | 497.1 |

TABLE 1-continued

| Example No. | Structure | Compound Name | Starting Materials | MW (MH+, 100%) |
|---|---|---|---|---|
| 11 | 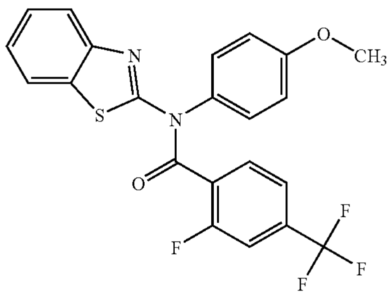 | N-Benzothiazol-2-yl-2-chloro-4-fluoro-N-(4-methoxy-phenyl)-benzamide | Benzothiazol-2-yl-(4-methoxy-phenyl)-amine and 2-Chloro-4-fluoro-benzoyl chloride (commercially available) | 413.1 |
| 12 | 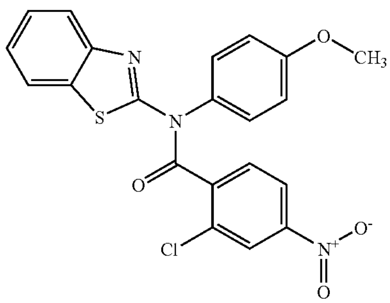 | N-Benzothiazol-2-yl-2-chloro-N-(4-methoxy-phenyl)-4-nitro-benzamide | Benzothiazol-2-yl-(4-methoxy-phenyl)-amine and 2-Chloro-4-nitro-benzoyl chloride (commercially available) | 440.2 |
| 13 | 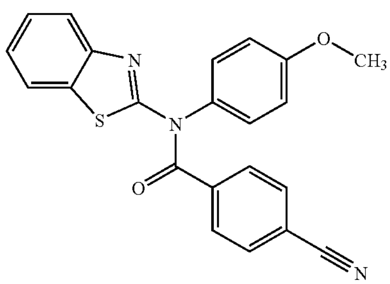 | N-Benzothiazol-2-yl-4-cyano-N-(4-methoxy-phenyl)-benzamide | Benzothiazol-2-yl-(4-methoxy-phenyl)-amine and 4-cyano-benzoyl chloride (commercially available) | 386.2 |
| 14 | 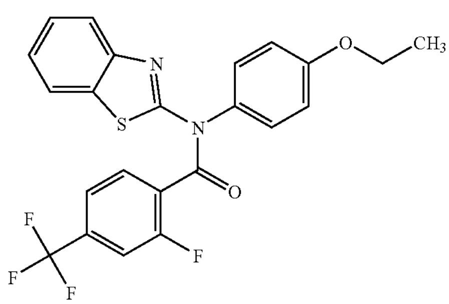 | N-Benzothiazol-2-yl-N-(4-ethoxy-phenyl)-2-fluoro-4-trifluoromethyl-benzamide | Benzothiazol-2-yl-(4-ethoxy-phenyl)-amine and 2-Fluoro-4-trifluoromethyl-benzoyl chloride (commercially available) | 461.2 |
| 15 | 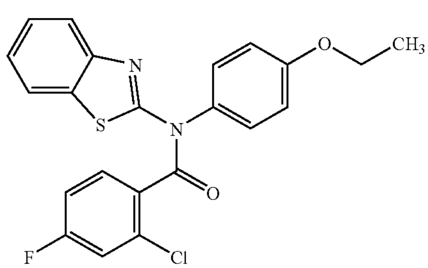 | N-Benzothiazol-2-yl-2-chloro-N-(4-ethoxy-phenyl)-4-fluoro-benzamide | Benzothiazol-2-yl-(4-ethoxy-phenyl)-amine and and 2-Chloro-4-fluoro-benzoyl chloride (commercially available) | 427.3 |

TABLE 1-continued

| Example No. | Structure | Compound Name | Starting Materials | MW (MH+, 100%) |
|---|---|---|---|---|
| 16 | 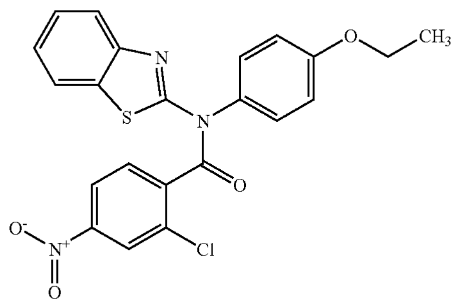 | N-Benzothiazol-2-yl-2-chloro-N-(4-ethoxy-phenyl)-4-nitro-benzamide | Benzothiazol-2-yl-(4-ethoxy-phenyl)-amine and 2-Chloro-4-nitro-benzoyl chloride (commercially available) | 454.3 |
| 17 | 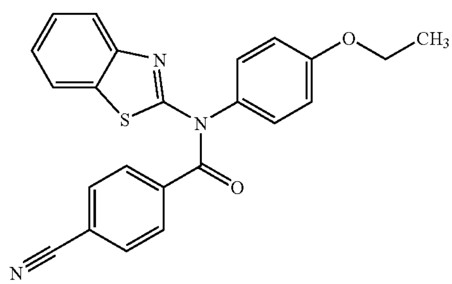 | N-Benzothiazol-2-yl-4-cyano-N-(4-ethoxy-phenyl)-benzamide | Benzothiazol-2-yl-(4-ethoxy-phenyl)-amine and 4-cyano-benzoyl chloride (commercially available) | 400.3 |
| 18 | 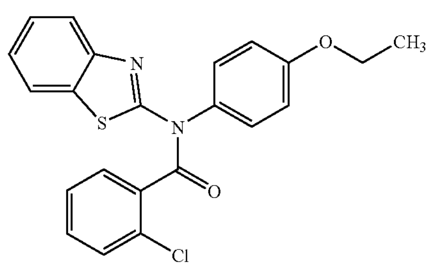 | N-Benzothiazol-2-yl-2-chloro-N-(4-ethoxy-phenyl)-benzamide | Benzothiazol-2-yl-(4-ethoxy-phenyl)-amine and 2-Chloro-benzoyl chloride (commercially available) | 409.2 |
| 19 | 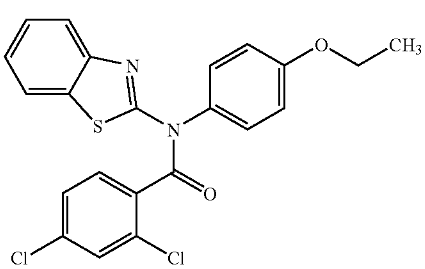 | N-Benzothiazol-2-yl-2,4-dichloro-N-(4-ethoxy-phenyl)-benzamide | Benzothiazol-2-yl-(4-ethoxy-phenyl)-amine and 2,4-Dichloro-benzoyl chloride (commercially available) | 443.1 |
| 20 | 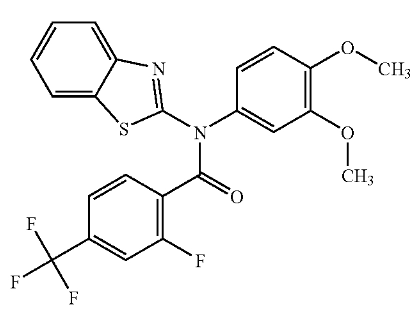 | N-Benzothiazol-2-yl-N-(3,4-dimethoxy-phenyl)-2-fluoro-4-trifluoromethyl-benzamide | Benzothiazol-2-yl-(3,4-dimethoxy-phenyl)-amine and 2-Fluoro-4-trifluoromethyl-benzoyl chloride (commercially available) | 477.2 |

TABLE 1-continued

| Example No. | Structure | Compound Name | Starting Materials | MW (MH+, 100%) |
|---|---|---|---|---|
| 21 | 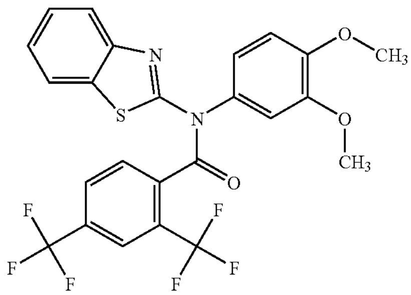 | N-Benzothiazol-2-yl-N-(3,4-dimethoxy-phenyl)-2,4-bis-trifluoromethyl-benzamide | Benzothiazol-2-yl-(3,4-dimethoxy-phenyl)-amine and 2,4-Bis-trifluoromethyl-benzoyl chloride (commercially available) | 527.2 |
| 22 | 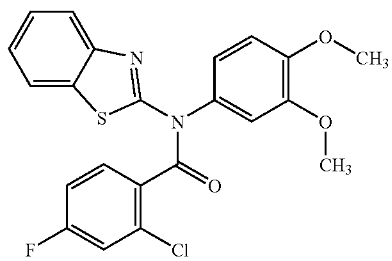 | N-Benzothiazol-2-yl-2-chloro-N-(3,4-dimethoxy-phenyl)-4-fluoro-benzamide | Benzothiazol-2-yl-(3,4-dimethoxy-phenyl)-amine and 2-Chloro-4-fluoro-benzoyl chloride (commercially available) | 443.2 |
| 23 | 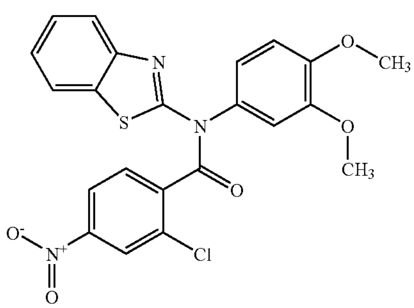 | N-Benzothiazol-2-yl-2-chloro-N-(3,4-dimethoxy-phenyl)-4-nitro-benzamide | Benzothiazol-2-yl-(3,4-dimethoxy-phenyl)-amine and 2-Chloro-4-nitro-benzoyl chloride (commercially available) | 469.9 |
| 24 | 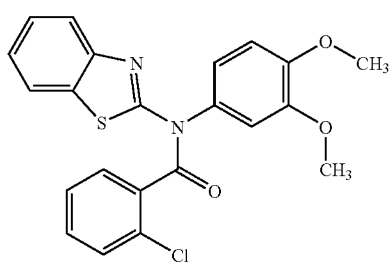 | N-Benzothiazol-2-yl-2-chloro-N-(3,4-dimethoxy-phenyl)-benzamide | Benzothiazol-2-yl-(3,4-dimethoxy-phenyl)-amine and 2-Chloro-benzoyl chloride (commercially available) | 425.3 |
| 25 | 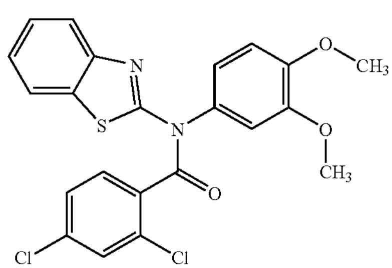 | N-Benzothiazol-2-yl-2,4-dichloro-N-(3,4-dimethoxy-phenyl)-benzamide | Benzothiazol-2-yl-(3,4-dimethoxy-phenyl)-amine and 2,4-Dichloro-benzoyl chloride (commercially available) | 461.2 |

TABLE 1-continued

| Example No. | Structure | Compound Name | Starting Materials | MW (MH+, 100%) |
|---|---|---|---|---|
| 26 | 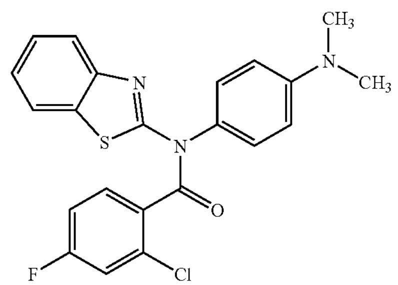 | N-Benzothiazol-2-yl-2-chloro-N-(4-dimethylamino-phenyl)-4-fluoro-benzamide | N-Benzothiazol-2-yl-N',N'-dimethyl-benzene-1,4-diamine and 2-Chloro-4-fluoro-benzoyl chloride (commercially available) | 426.3 |
| 27 | 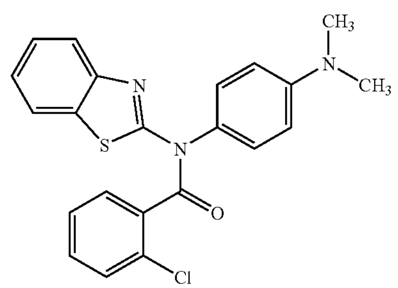 | N-Benzothiazol-2-yl-2-chloro-N-(4-dimethylamino-phenyl)-benzamide | N-Benzothiazol-2-yl-N',N'-dimethyl-benzene-1,4-diamine and 2-Chloro-benzoyl chloride (commercially available) | 408.2 |
| 28 | 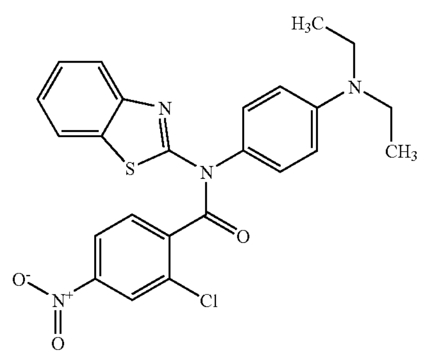 | N-Benzothiazol-2-yl-2-chloro-N-(4-diethylamino-phenyl)-4-nitro-benzamide | N-Benzothiazol-2-yl-N',N'-diethyl-benzene-1,4-diamine and 2-Chloro-4-nitro-benzoyl chloride (commercially available) | 481.3 |
| 29 | 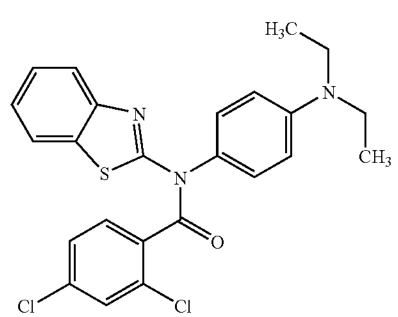 | N-Benzothiazol-2-yl-2,4-dichloro-N-(4-diethylamino-phenyl)-benzamide | N-Benzothiazol-2-yl-N',N'-diethyl-benzene-1,4-diamine and 2,4-Dichloro-benzoyl chloride (commercially available) | 470.1 |
| 30 | 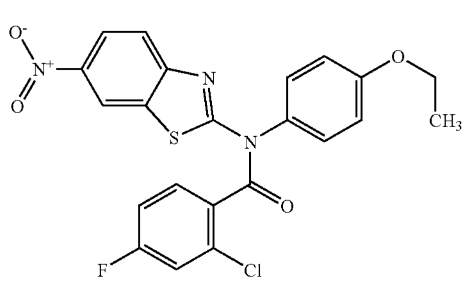 | 2-Chloro-N-(4-ethoxy-phenyl)-4-fluoro-N-(6-nitro-benzothiazol-2-yl)-benzamide | (4-Ethoxy-phenyl)-(6-nitro-benzothiazol-2-yl)-amine and 2-Chloro-4-fluoro-benzoyl chloride (commercially available) | 472.1 |

TABLE 1-continued

| Example No. | Structure | Compound Name | Starting Materials | MW (MH+, 100%) |
|---|---|---|---|---|
| 31 | 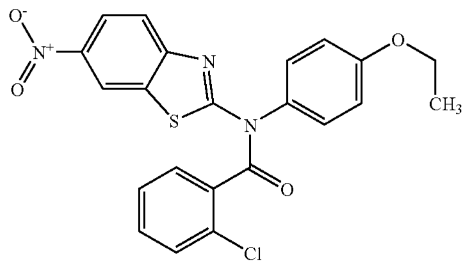 | 2-Chloro-N-(4-ethoxy-phenyl)-N-(6-nitro-benzothiazol-2-yl)-benzamide | (4-Ethoxy-phenyl)-(6-nitro-benzothiazol-2-yl)-amine and 2-Chloro-benzoyl chloride (commercially available) | 454.3 |
| 32 | 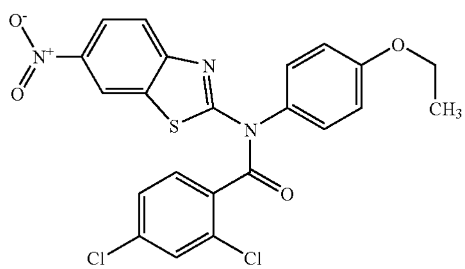 | 2,4-Dichloro-N-(4-ethoxy-phenyl)-N-(6-nitro-benzothiazol-2-yl)-benzamide | (4-Ethoxy-phenyl)-(6-nitro-benzothiazol-2-yl)-amine and 2,4-Dichloro-benzoyl chloride (commercially available) | 488.2 |
| 33 | 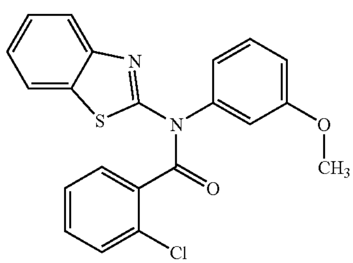 | N-Benzothiazol-2-yl-2-chloro-N-(3-methoxy-phenyl)-benzamide | Benzothiazol-2-yl-(3-methoxy-phenyl)-amine and 2-Chloro-benzoyl chloride (commercially available) | 395.2 |
| 34 | 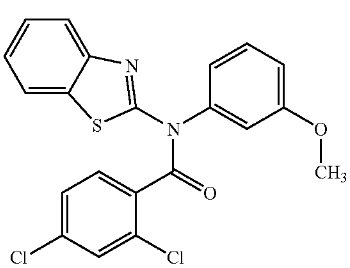 | N-Benzothiazol-2-yl-2,4-dichloro-N-(3-methoxy-phenyl)-benzamide | Benzothiazol-2-yl-(3-methoxy-phenyl)-amine and 2,4-Dichloro-benzoyl chloride (commercially available) | 429.3 |

Example 35

N-Benzothiazol-2-yl-2-chloro-N-(3-methoxy-4-methyl-phenyl)-benzamide

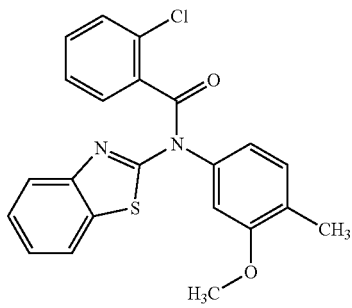

A mixture of 0.339 g (2 mmol) 2-Chlorobenzthiazole (commercially available) and 0.275 g (2 mmol) 3-methoxy-4-methylaniline (commercially available) in 4 ml acetic acid was heated to 115° C. for 4 h. After cooling to room temperature the mixture was subjected to preparative HPLC separation on reversed phase eluting with an acetonitrile/water gradient. The product fractions of Benzothiazol-2-yl-(3-methoxy-4-methyl-phenyl)-amine were evaporated to dryness and reacted according to the procedure described for Example 2 with 2-chlorobenzoyl chloride to yield the title compound. MS (m/e): 409.3 (MH$^+$, 100%). According to the procedure described for Example 35 further N-Benzothiazol-2-yl-N-(aryl)-benzamide derivatives have been synthesised by reaction of 2-chlorobenzthiazole with the respective aniline (commercially available) and subsequently with the respective acid chloride. The results are shown in table 2 below and comprise Example 36 to Example 43.

TABLE 2

| Example No. | Structure | Compound Name | Starting Materials | MW (MH$^+$, 100%) |
|---|---|---|---|---|
| 36 | 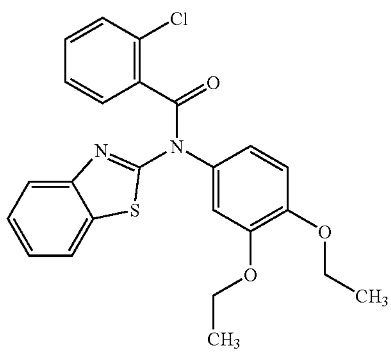 | N-Benzothiazol-2-yl-2-chloro-N-(3,4-diethoxy-phenyl)-benzamide | Benzothiazol-2-yl-(3,4-diethoxy-phenyl)-amine and 2-Chloro-benzoyl chloride (commercially available) | 453.4 |
| 37 | 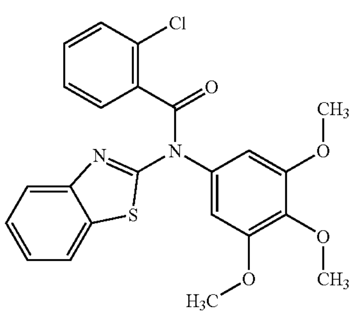 | N-Benzothiazol-2-yl-2-chloro-N-(3,4,5-trimethoxy-phenyl)-benzamide | Benzothiazol-2-yl-(3,4,5-trimethoxy-phenyl)-amine and 2-Chloro-benzoyl chloride (commercially available) | 455.4 |
| 38 | 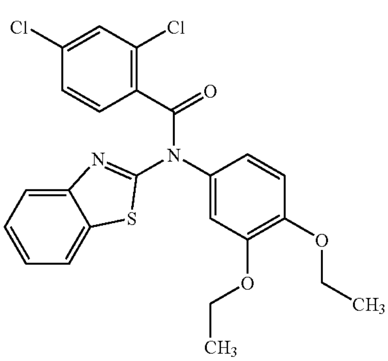 | N-Benzothiazol-2-yl-2,4-dichloro-N-(3,4-diethoxy-phenyl)-benzamide | Benzothiazol-2-yl-(3,4-diethoxy-phenyl)-amine and 2,4-Dichloro-benzoyl chloride (commercially available) | 487.2 |

TABLE 2-continued

| Example No. | Structure | Compound Name | Starting Materials | MW (MH+, 100%) |
|---|---|---|---|---|
| 39 | 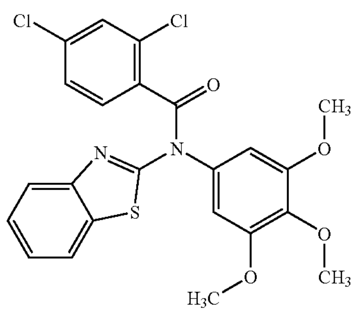 | N-Benzothiazol-2-yl-2,4-dichloro-N-(3,4,5-trimethoxy-phenyl)-benzamide | Benzothiazol-2-yl-(3,4,5-trimethoxy-phenyl)-amine and 2,4-Dichloro-benzoyl chloride (commercially available) | 489.2 |
| 40 | 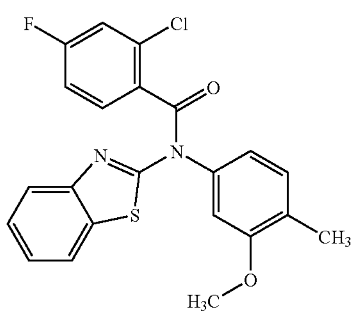 | N-Benzothiazol-2-yl-2-chloro-4-fluoro-N-(3-methoxy-4-methyl-phenyl)-benzamide | Benzothiazol-2-yl-(3-methoxy-4-methyl-phenyl)-amine and 2-Chloro-4-fluoro-benzoyl chloride (commercially available) | 427.3 |
| 41 | 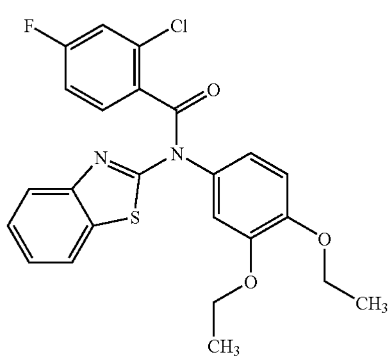 | N-Benzothiazol-2-yl-2-chloro-N-(3,4-diethoxy-phenyl)-4-fluoro-benzamide | Benzothiazol-2-yl-(3,4-diethoxy-phenyl)-amine and 2-Chloro-4-fluoro-benzoyl chloride (commercially available) | 471.2 |
| 42 | 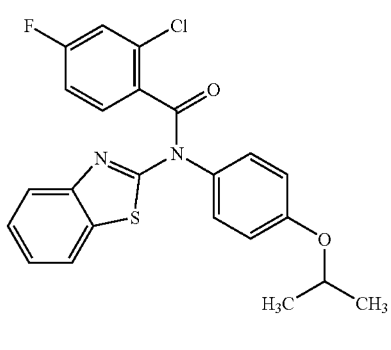 | N-Benzothiazol-2-yl-2-chloro-4-fluoro-N-(4-isopropoxy-phenyl)-benzamide | Benzothiazol-2-yl-(4-isopropoxy-phenyl)-amine and 2-Chloro-4-fluoro-benzoyl chloride (commercially available) | 441.3 |

TABLE 2-continued

| Example No. | Structure | Compound Name | Starting Materials | MW (MH+, 100%) |
|---|---|---|---|---|
| 43 | 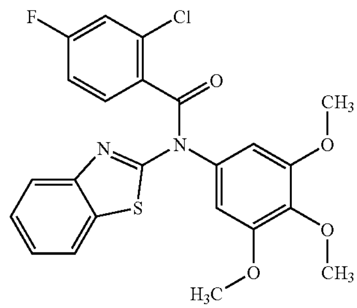 | N-Benzothiazol-2-yl-2-chloro-4-fluoro-N-(3,4,5-trimethoxy-phenyl)-benzamide | Benzothiazol-2-yl-(3,4,5-trimethoxy-phenyl)-amine and 2-Chloro-4-fluoro-benzoyl chloride (commercially available) | 473.1 |

Example 44

2,4-Dichloro-N-(3,4-dimethoxy-phenyl)-N-(6-nitro-benzothiazol-2-yl)-benzamide

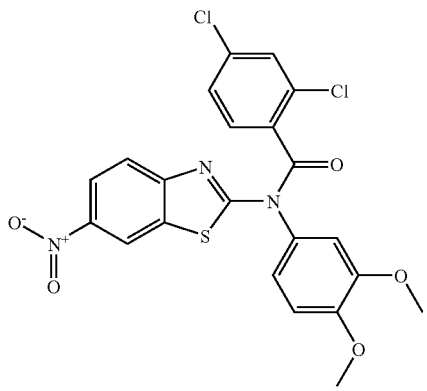

The title compound was synthesised from (3,4-Dimethoxy-phenyl)-(6-nitro-benzothiazol-2-yl)-amine and 2,4-dichlorobenzoyl chloride (commercially available) according to the procedure described for Example 2. MS (m/e): 504.1 (MH+, 100%).

Example 45

N-(6-Amino-benzothiazol-2-yl)-2,4-dichloro-N-(3,4-dimethoxy-phenyl)-benzamide

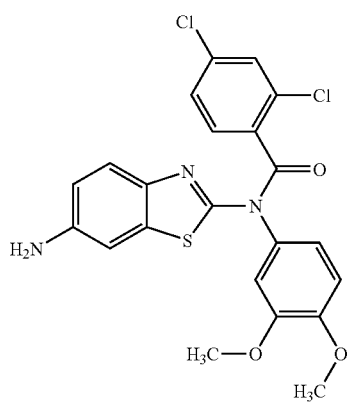

A mixture of 2 g (3.97 mmol) 2,4-Dichloro-N-(3,4-dimethoxy-phenyl)-N-(6-nitro-benzothiazol-2-yl)-benzamide in 25 ml DMF and 4 ml 1N HCl was treated with 2.24 g tin(II) chloride dihydrate and heated to 80° C. for 4 h. After cooling to room temperature 50 ml saturated NaHCO$_3$ was added and the mixture was extracted with ethyl acetate. The organic phase is treated with decalit and filtered. The organic phase of the filtrate was washed with saturated NaCl, dried with MgSO$_4$, filtered and evaporated to dryness. The residue was purified on reversed phase preparative HPLC eluting with an acetonitrile/water gradient to obtain 536 mg (29%) of the title compound as yellowish amorphous solid. MS (m/e): 474.0 (MH+, 100%).

Example 46

2,4-Dichloro-N-(3,4-dimethoxy-phenyl)-N-(6-methanesulfonylamino-benzothiazol-2-yl)-benzamide

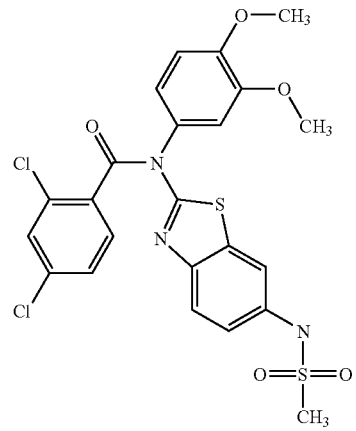

A mixture of 33.2 mg (0.07 mmol) N-(6-Amino-benzothiazol-2-yl)-2,4-dichloro-N-(3,4-dimethoxy-phenyl)-benzamide in 0.7 ml DCM, 18.2 mg (0.18 mmol) NEt$_3$ and 10.3 mg (0.091 mmol) methanesulfonyl chloride in 0.2 ml DCM was reacted for 16 h at room temperature. After evaporation of all volatiles the residue was taken up in DMF/acetonitrile and subjected to preparative HPLC separation on reversed phase eluting with an acetonitrile/water gradient to yield 9.6 mg (25%) of the title compound. MS (m/e): 552.1 (MH+, 100%).

According to the procedure described for the synthesis of Example 46 2,4-Dichloro-N-(3,4-dimethoxy-phenyl)-6-amido-benzothiazol-2-yl)-benzamide or 2,4-Dichloro-N-(3,4-dimethoxy-phenyl)-6-sulfonamido-benzothiazol-2-yl)-benzamide derivatives have been synthesised from N-(6-Amino-benzothiazol-2-yl)-2,4-dichloro-N-(3,4-dimethoxy-phenyl)-benzamide and sulfonylchlorides or acid chlorides (commercially available). The results are shown in table 3 below and comprise Example 47 to Example 52.

TABLE 3

| Example No. | Structure | Compound Name | Starting Materials | MW (MH+, 100%) |
|---|---|---|---|---|
| 47 | 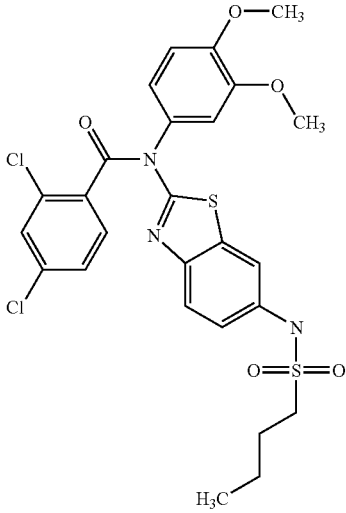 | N-[6-(Butane-1-sulfonylamino)-benzothiazol-2-yl]-2,4-dichloro-N-(3,4-dimethoxy-phenyl)-benzamide | N-(6-Amino-benzothiazol-2-yl)-2,4-dichloro-N-(3,4-dimethoxy-phenyl)-benzamide and butyl sulfonyl chloride | 594.2 |
| 48 | 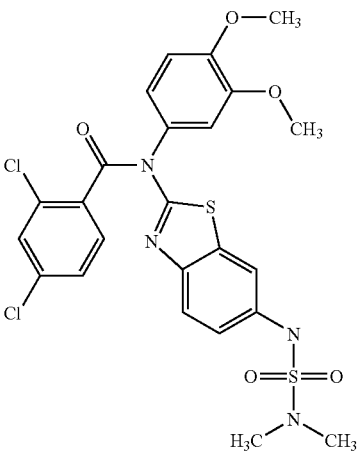 | N-[6-(Dimethylamino-1-sulfonylamino)-benzothiazol-2-yl]-2,4-dichloro-N-(3,4-dimethoxy-phenyl)-benzamide | N-(6-Amino-benzothiazol-2-yl)-2,4-dichloro-N-(3,4-dimethoxy-phenyl) benzamide and dimetyhlamino sulfonyl chloride | 581.2 |

TABLE 3-continued

| Example No. | Structure | Compound Name | Starting Materials | MW (MH+, 100%) |
|---|---|---|---|---|
| 49 | 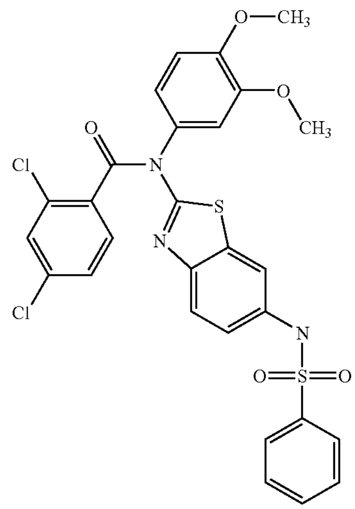 | N-(6-Benzenesulfonylamino-benzothiazol-2-yl)-2,4-dichloro-N-(3,4-dimethyoxy-phenyl)-benzamide | N-(6-Amino-benzothiazol-2-yl)-2,4-dichloro-N-(3,4-dimethoxy-phenyl)-benzamide and Benzenesulfonyl chloride | 614.1 |
| 50 | 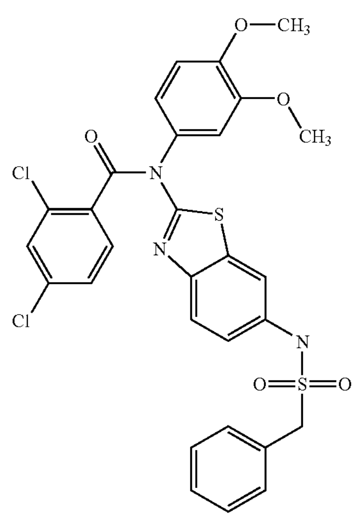 | 2,4-Dichloro-N-(3,4-dimethoxy-phenyl)-N-(6-phenylmethanesulfonylamino-benzothiazol-2-yl]-benzamide | N-(6-Amino-benzothiazol-2-yl)-2,4-dichloro-N-(3,4-dimethoxy-phenyl)-benzamide and Phenyl-methanesulfonyl chloride | 628.1 |

TABLE 3-continued

| Example No. | Structure | Compound Name | Starting Materials | MW (MH+, 100%) |
|---|---|---|---|---|
| 51 | 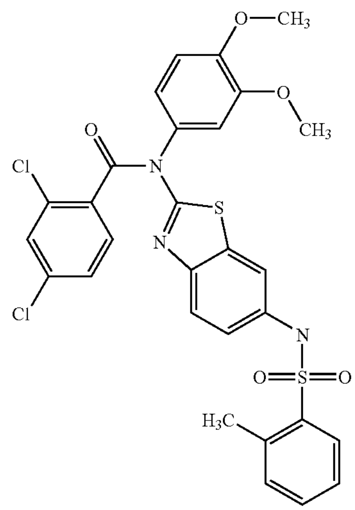 | 2,4-Dichloro-N-(3,4-dimethoxy-phenyl)-N-[6-(toluene-2-sulfonylamino)-benzothiazol-2-yl]-benzamide | N-(6-Amino-benzothiazol-2-yl)-2,4-dichloro-N-(3,4-dimethoxy-phenyl)-benzamide and 2-Methyl-benzenesulfonyl chloride | 628.1 |
| 52 | 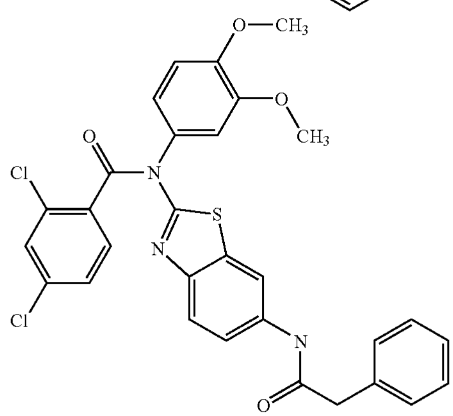 | 2,4-Dichloro-N-(3,4-dimethoxy-phenyl)-N-(6-phenylacetylamino-benzothiazol-2-yl)-benzamide | N-(6-Amino-benzothiazol-2-yl)-2,4-dichloro-N-(3,4-dimethoxy-phenyl)-benzamide and Phenyl-acetyl chloride | 592.2 |

Example 53

2-Chloro-N-(3,4-dimethoxy-phenyl)-N-(6-nitro-benzothiazol-2-yl)-benzamide

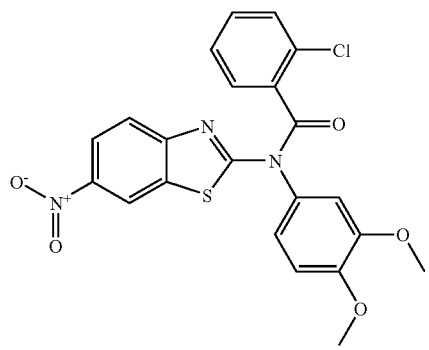

The title compound was synthesised from (3,4-Dimethoxy-phenyl)-(6-nitro-benzothiazol-2-yl)-amine and 2-chlorobenzoyl chloride (commercially available) according to the procedure described for Example 2. MS (m/e): 469.7 (MH+, 100%).

Example 54

N-(6-Amino-benzothiazol-2-yl)-2-chloro-N-(3,4-dimethoxy-phenyl)-benzamide

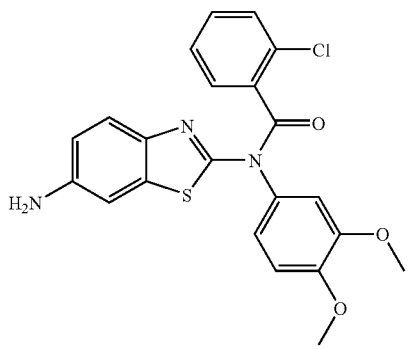

The title compound was synthesised from 2-Chloro-N-(3,4-dimethoxy-phenyl)-N-(6-nitro-benzothiazol-2-yl)-benzamide according to the procedure described for Example 45. MS (m/e): 440.1 (MH+, 100%).

According to the procedure described for the synthesis of Example 46 2-Chloro-N-(3,4-dimethoxy-phenyl)-6-amido-benzothiazol-2-yl)-benzamide or 2-Chloro-N-(3,4-dimethoxy-phenyl)-6-sulfonamido-benzothiazol-2-yl)-benzamide derivatives have been synthesised from N-(6-Amino-benzothiazol-2-yl)-2-chloro-N-(3,4-dimethoxy-phenyl)-benzamide and sulfonylchlorides or acid chlorides (commercially available). The results are shown in table 4 below and comprise Example 55 to Example 61.

TABLE 4

| Example No. | Structure | Compound Name | Starting Materials | MW (MH+, 100%) |
|---|---|---|---|---|
| 55 | 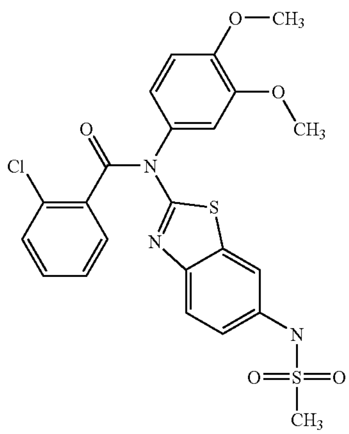 | 2-Chloro-N-(3,4-dimethoxy-phenyl)-N-(6-methanesulfonylamino-benzothiazol-2-yl)-benzamide | N-(6-Amino-benzothiazol-2-yl)-2-chloro-N-(3,4-dimethoxy-phenyl)-benzamide and methane sulfonyl chloride | 518.2 |
| 56 | 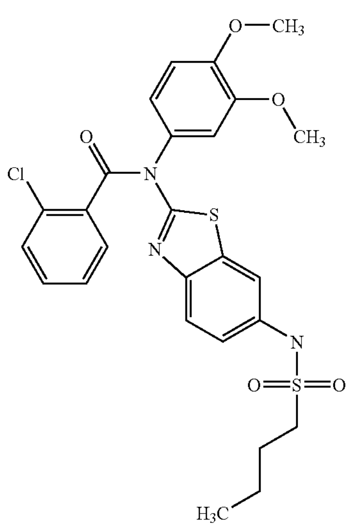 | N-[6-(Butane-1-sulfonylamino)-benzothiazol-2-yl]-2-chloro-N-(3,4-dimethoxy-phenyl)-benzamide | N-(6-Amino-benzothiazol-2-yl)-2-chloro-N-(3,4-dimethoxy-phenyl)-benzamide and butane sulfonyl chloride | 560.2 |

TABLE 4-continued

| Example No. | Structure | Compound Name | Starting Materials | MW (MH+, 100%) |
|---|---|---|---|---|
| 57 | 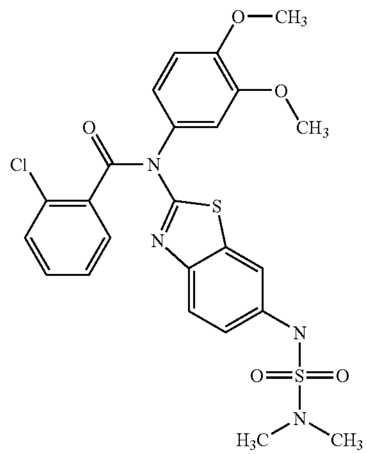 | N-[6-(Dimethylamino-1-sulfonylamino)-benzothiazol-2-yl]-2-chloro-N-(3,4-dimethoxy-phenyl)-benzamide | N-(6-Amino-benzothiazol-2-yl)-2-chloro-N-(3,4-dimethoxy-phenyl) benzamide and dimetyhlamino sulfonyl chloride | 547.2 |
| 58 | 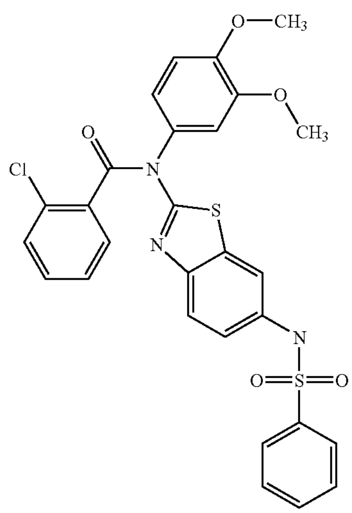 | N-(6-Benzenesulfonylamino-benzothiazol-2-yl)-2-chloro-N-(3,4-dimethoxy-phenyl)-benzamide | N-(6-Amino-benzothiazol-2-yl)-2-chloro-N-(3,4-dimethoxy-phenyl)-benzamide and Benzenesulfonyl chloride | 580.2 |
| 59 | 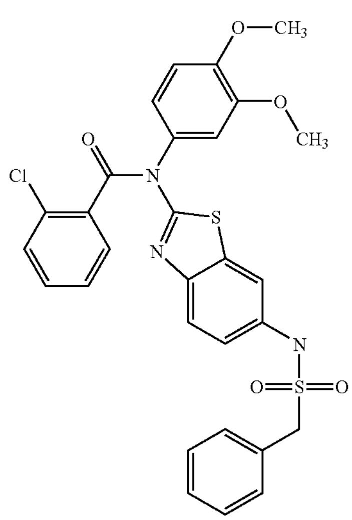 | 2-Chloro-N-(3,4-dimethoxy-phenyl)-N-(6-phenylmethanesulfonylamino-benzothiazol-2-yl)-benzamide | N-(6-Amino-benzothiazol-2-yl)-2-chloro-N-(3,4-dimethoxy-phenyl)-benzamide and Phenyl-methanesulfonyl chloride | 594.2 |

TABLE 4-continued

| Example No. | Structure | Compound Name | Starting Materials | MW (MH+, 100%) |
|---|---|---|---|---|
| 60 | 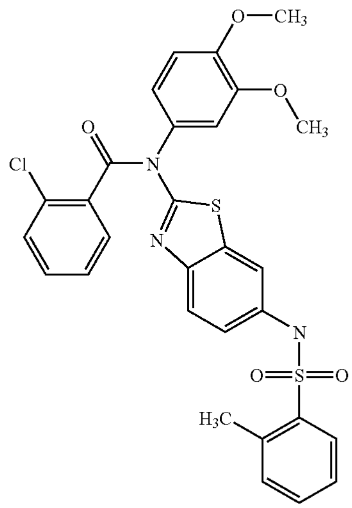 | 2-Chloro-N-(3,4-dimethoxy-phenyl)-N-[6-(toluene-2-sulfonylamino)-benzothiazol-2-yl]-benzamide | N-(6-Amino-benzothiazol-2-yl)-2-chloro-N-(3,4-dimethoxy-phenyl)-benzamide and 2-Methyl-benzenesulfonyl chloride | 594.2 |
| 61 | 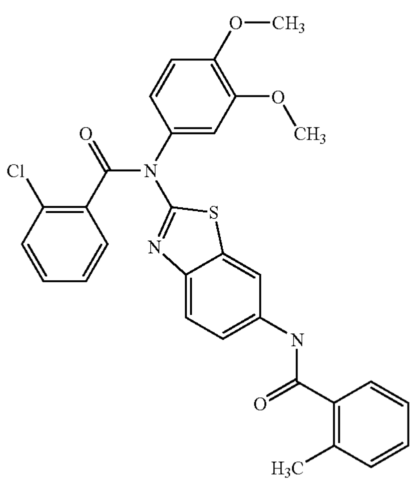 | N-(6-(2-methylbenzoyl-amino)-benzothiazol-2-yl)-2-chloro-N-(3,4-dimethoxy-phenyl)-benzamide | N-(6-Amino-benzothiazol-2-yl)-2-chloro-N-(3,4-dimethoxy-phenyl)-benzamide and 2-Methyl-benzoyl chloride | 558.2 |

Example 62

N-Benzothiazol-2-yl-2-chloro-N-(4-trifluoromethoxy-phenyl)-benzamide

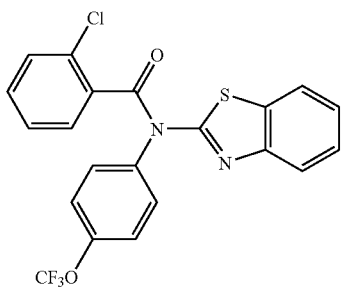

To 0.2 g (0.6 mmol) benzothiazol-2-yl-(4-trifluoromethoxy-phenyl)-amine dissolved in tetrahydrofuran (5 mL), potassium-t-butylate (0.11 g, 1.0 mmol) and 2-chlorobenzoylchloride (0.13 g, 0.7 mmol) were added. The mixture was stirred for 3 h at room temperature. Water (10 mL) was added and the mixture was extracted with ethylacetate (2×20 mL). Organic phases were pooled, dried with MgSO$_4$ and yielded after evaporation and chromatography (silica gel; n-hexane/ethylacetate) the title compound (0.26 g; 89%). MS (m/z): 449.4 (MH+, 100%).

According to the procedure described for the synthesis of Example 61 benzothiazol-2-yl-benzamide derivatives have been synthesised from benzothiazol-2-yl-phenylamine derivatives and acid chlorides. The results are shown in table 5 below and comprise Example 63 to Example 67.

TABLE 5

| Example No. | Structure | Compound Name | Starting Materials | MW (MH+, 100%) |
|---|---|---|---|---|
| 63 | 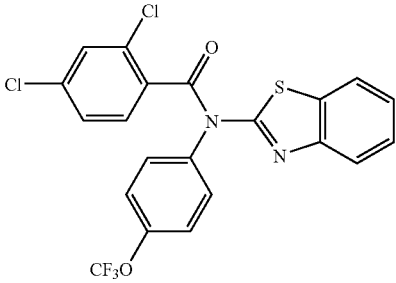 | N-Benzothiazol-2-yl-2,4-dichloro-N-(4-trifluoromethoxy-phenyl)-benzamide | benzothiazol-2-yl-(4-trifluoromethoxy-phenyl)-amine and 2,4-dichlorobenzoylchloride (commercially available) | 483.5 |
| 64 | 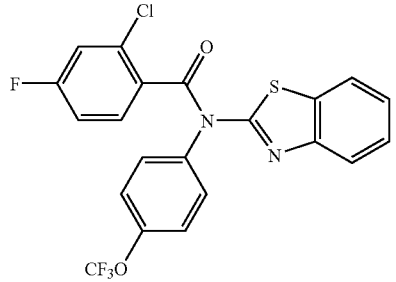 | N-Benzothiazol-2-yl-2-chloro-4-fluoro-N-(4-trifluoromethoxy-phenyl)-benzamide | benzothiazol-2-yl-(4-trifluoromethoxy-phenyl)-amine and 2-chloro-4-fluoro-benzoylchloride (commercially available) | 467.5 |
| 65 | 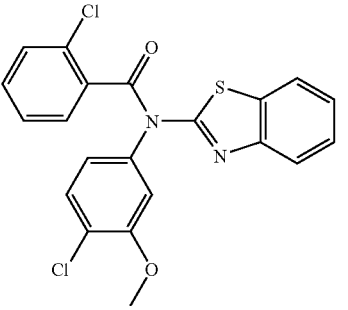 | N-Benzothiazol-2-yl-2-chloro-N-(4-chloro-3-methoxy-phenyl)-benzamide | benzothiazol-2-yl-(4-chloro-3-methoxy-phenyl)-amine and 2-chlorobenzoylchloride (commercially available) | 429.4 |
| 66 | 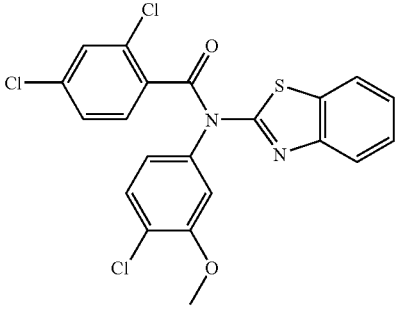 | N-Benzothiazol-2-yl-2,4-dichloro-N-(4-chloro-3-methoxy-phenyl)-benzamide | benzothiazol-2-yl-(4-chloro-3-methoxy-phenyl)-amine and 2,4-dichlorobenzoylchloride (commercially available) | 463.7 |
| 67 | 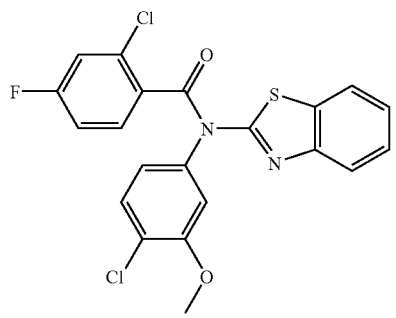 | N-Benzothiazol-2-yl-2-chloro-4-fluoro-N-(4-chloro-3-methoxy-phenyl)-benzamide | benzothiazol-2-yl-(4-trifluoromethoxy-phenyl)-amine and 2-chloro-4-fluoro-benzoylchloride (commercially available) | 447.4 |

GALENICAL EXAMPLES

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

| Injection solutions can have the following composition: | |
| --- | --- |
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

What is claimed is:

1. A compound of formula (I)

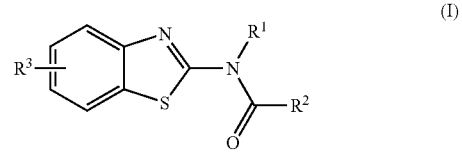

wherein
$R^1$ is phenyl mono-, di- or tri-substituted, independently, by a group selected from the group consisting of halogen and lower alkoxy;
$R^2$ is phenyl, or phenyl mono-, di- or tri-substituted, independently, by a group selected from the group consisting of halogen, halogenated-lower alkyl, nitro and cyano;
$R^3$ is hydrogen, lower alkyl, benzyl, lower alkoxy, halogen, cyano, nitro, amino, —$NHSO_2$—$R^{3a}$ or —NHCO—$R^{3b}$;
$R^{3a}$ is lower alkyl, di-lower alkylamino, benzyl, phenyl or phenyl mono-, di- or tri-substituted, independently, by lower alkyl;
$R^{3b}$ is benzyl, phenyl or phenyl mono-, di- or tri-substituted, independently, by lower alkyl;
or a pharmaceutically acceptable salt thereof.

2. The compound according to claim 1, wherein $R^1$ is 4-chloro-phenyl, 4-chloro-3-methoxy-phenyl or 3,4-dimethoxy-phenyl.

3. The compound according to claim 1, wherein $R^2$ is phenyl mono substituted with halogen.

4. The compound according to claim 2, wherein $R^2$ is 2-chloro-phenyl or 2,4-dichlorophenyl.

5. The compound according to claim 1, wherein $R^3$ is hydrogen, nitro, amino, —$NHSO_2$—$R^{3a}$ or —NHCO—$R^{3b}$.

6. The compound according to claim 5, wherein $R^3$ is hydrogen.

7. The compound according to claim 1, wherein substituent $R^3$ is at the 6-position of the benzthiazole ring.

8. The compound according to claim 5 in which $R^3$ is —$NHSO_2$—$R^{3a}$, wherein $R^{3a}$ is methyl, n-butyl, dimethylamino, benzyl, phenyl or phenyl mono-, di- or tri-substituted methyl.

9. The compound according to claim 5 in which $R^3$ is —NHCO—$R^{3b}$, wherein $R^{3b}$ is benzyl or phenyl mono-substituted by lower alkyl.

10. The compound of formula (I) according to claim 1, selected from the group consisting of:
N-benzothiazol-2-yl-2-chloro-N-(3,4-dimethoxy-phenyl)-4-nitro-benzamide;
N-benzothiazol-2-yl-2-chloro-N-(3,4-dimethoxy-phenyl)-benzamide;
N-benzothiazol-2-yl-2,4-dichloro-N-(3,4-dimethoxy-phenyl)-benzamide;
N-benzothiazol-2-yl-2-chloro-N-(3,4-diethoxy-phenyl)-benzamide; and
N-benzothiazol-2-yl-2-chloro-N-(3,4,5-trimethoxy-phenyl)-benzamide;
or a pharmaceutically acceptable salt thereof.

11. The compound of formula (I) according to claim 1, selected from the group consisting of:
N-benzothiazol-2-yl-2,4-dichloro-N-(3,4-diethoxy-phenyl)-benzamide;

N-benzothiazol-2-yl-2-chloro-N-(3,4-diethoxy-phenyl)-4-fluoro-benzamide;
N-benzothiazol-2-yl-2-chloro-4-fluoro-N-(4-isopropoxy-phenyl)-benzamide;
N-benzothiazol-2-yl-2-chloro-N-(4-chloro-3-methoxy-phenyl)-benzamide;
N-benzothiazol-2-yl-2,4-dichloro-N-(4-chloro-3-methoxy-phenyl)-benzamide; and
N-benzothiazol-2-yl-2-chloro-4-fluoro-N-(4-chloro-3-methoxy-phenyl)-benzamide;
or a pharmaceutically acceptable salt thereof.

12. The compound of formula (I) in accordance with claim 1, selected from the group consisting of:
N-benzothiazol-2-yl-2-chloro-N-(4-chloro-phenyl)-benzamide;
N-benzothiazol-2-yl-2-chloro-N-(3,5-dichloro-phenyl)-benzamide;
N-benzothiazol-2-yl-2-chloro-N-(3,4-dichloro-phenyl)-benzamide;
N-benzothiazol-2-yl-2,4-dichloro-N-(3,4-dichloro-phenyl)-benzamide;
N-benzothiazol-2-yl-2-chloro-N-(4-methoxy-phenyl)-benzamide;
N-benzothiazol-2-yl-2,4-dichloro-N-(4-methoxy-phenyl)-benzamide;
N-benzothiazol-2-yl-2-fluoro-N-(4-methoxy-phenyl)-4-trifluoromethyl-benzamide;
N-benzothiazol-2-yl-N-(4-methoxy-phenyl)-2,4-bis-trifluoromethyl-benzamide; and
N-benzothiazol-2-yl-2-chloro-4-fluoro-N-(4-methoxy-phenyl)-benzamide;
or a pharmaceutically acceptable salt thereof.

13. The compound of formula (I) in accordance with claim 1, selected from the group consisting of:
N-benzothiazol-2-yl-2-chloro-N-(4-methoxy-phenyl)-4-nitro-benzamide;
N-benzothiazol-2-yl-4-cyano-N-(4-methoxy-phenyl)-benzamide;N-benzothiazol-2-yl-N-(4-ethoxy-phenyl)-2-fluoro-4-trifluoromethyl-benzamide;
N-benzothiazol-2-yl-2-chloro-N-(4-ethoxy-phenyl)-4-fluoro-benzamide;
N-benzothiazol-2-yl-2-chloro-N-(4-ethoxy-phenyl)-4-nitro-benzamide;
N-benzothiazol-2-yl-4-cyano-N-(4-ethoxy-phenyl)-benzamide;
N-benzothiazol-2-yl-2-chloro-N-(4-ethoxy-phenyl)-benzamide;
N-benzothiazol-2-yl-2,4-dichloro-N-(4-ethoxy-phenyl)-benzamide;
N-benzothiazol-2-yl-N-(3,4-dimethoxy-phenyl)-2-fluoro-4-trifluoromethyl-benzamide; and
N-benzothiazol-2-yl-N-(3,4-dimethoxy-phenyl)-2,4-bis-trifluoromethyl-benzamide;
or a pharmaceutically acceptable salt thereof.

14. The compound of formula (I) in accordance with claim 1, selected from the group consisting of:
N-benzothiazol-2-yl-2-chloro-N-(3,4-dimethoxy-phenyl)-4-fluoro-benzamide;
N-benzothiazol-2-yl-2-chloro-N-(3,4-dimethoxy-phenyl)-4-nitro-benzamide;
N-benzothiazol-2-yl-2-chloro-N-(3,4-dimethoxy-phenyl)-benzamide;
N-benzothiazol-2-yl-2,4-dichloro-N-(3,4-dimethoxy-phenyl)-benzamide;
2-chloro-N-(4-ethoxy-phenyl)-4-fluoro-N-(6-nitro-benzothiazol-2-yl)-benzamide; and
2-chloro-N-(4-ethoxy-phenyl)-N-(6-nitro-benzothiazol-2-yl)-benzamide;
or a pharmaceutically acceptable salt thereof.

15. The compound of formula (I) in accordance with claim 1, selected from the group consisting of:
2,4-dichloro-N-(4-ethoxy-phenyl)-N-(6-nitro-benzothiazol-2-yl)-benzamide;
N-benzothiazol-2-yl-2-chloro-N-(3-methoxy-phenyl)-benzamide;
N-benzothiazol-2-yl-2,4-dichloro-N-(3-methoxy-phenyl)-benzamide;
N-benzothiazol-2-yl-2-chloro-N-(3,4-diethoxy-phenyl)-benzamide;
N-benzothiazol-2-yl-2,4-dichloro-N-(3,4-diethoxy-phenyl)-benzamide; and
N-benzothiazol-2-yl-2-chloro-N-(3,4-diethoxy-phenyl)-4-fluoro-benzamide;
or a pharmaceutically acceptable salt thereof.

16. The compound of formula (I) in accordance with claim 1, selected from the group consisting of:
N-benzothiazol-2-yl-2-chloro-4-fluoro-N-(4-isopropoxy-phenyl)-benzamide;
2,4-dichloro-N-(3,4-dimethoxy-phenyl)-N-(6-nitro-benzothiazol-2-yl)-benzamide;
N-(6-amino-benzothiazol-2-yl)-2,4-dichloro-N-(3,4-dimethoxy-phenyl)-benzamide;
2,4-dichloro-N-(3,4-dimethoxy-phenyl)-N-(6-methanesulfonylamino-benzothiazol-2-yl)-benzamide;
N-[6-(butane-1-sulfonylamino)-benzothiazol-2-yl]-2,4-dichloro-N-(3,4-dimethoxy-phenyl)-benzamide;
N-[6-(dimethylamino-1-sulfonylamino)-benzothiazol-2-yl]-2,4-dichloro-N-(3,4-dimethoxy-phenyl)-benzamide;
N-(6-benzenesulfonylamino-benzothiazol-2-yl)-2,4-dichloro-N-(3,4-dimethoxy-phenyl)-benzamide;
2,4-dichloro-N-(3,4-dimethoxy-phenyl)-N-(6-phenyl-methanesulfonylamino-benzothiazol-2-yl)-benzamide; and
2,4-dichloro-N-(3,4-dimethoxy-phenyl)-N-[6-(toluene-2-sulfonylamino)-benzothiazol-2-yl]-benzamide;
or a pharmaceutically acceptable salt thereof.

17. The compound of formula (I) in accordance with claim 1, selected from the group consisting of:
2,4-dichloro-N-(3,4-dimethoxy-phenyl)-N-(6-phenylacetylamino-benzothiazol-2-yl)-benzamide;
2-chloro-N-(3,4-dimethoxy-phenyl)-N-(6-nitro-benzothiazol-2-yl)-benzamide;
N-(6-amino-benzothiazol-2-yl)-2-chloro-N-(3,4-dimethoxy-phenyl)-benzamide;
2-chloro-N-(3,4-dimethoxy-phenyl)-N-(6-methanesulfonylamino-benzothiazol-2-yl)-benzamide;
N-[6-(butane-1-sulfonylamino)-benzothiazol-2-yl]-2-chloro-N-(3,4-dimethoxy-phenyl)-benzamide;
N-[6-(dimethylamino-1-sulfonylamino)-benzothiazol-2-yl]-2-chloro-N-(3,4-dimethoxy-phenyl)-benzamide;
N-(6-benzenesulfonylamino-benzothiazol-2-yl)-2-chloro-N-(3,4-dimethoxy-phenyl)-benzamide;
2-chloro-N-(3,4-dimethoxy-phenyl)-N-(6-phenyl-methanesulfonylamino-benzothiazol-2-yl)-benzamide; and
2-chloro-N-(3,4-dimethoxy-phenyl)-N-[6-(toluene-2-sulfonylamino)-benzothiazol-2-yl]-benzamide;
or a pharmaceutically acceptable salt thereof.

18. The compound of formula (I) in accordance with claim 1, selected from the group consisting of:
N-(6-(2-methylbenzoylamino)-benzothiazol-2-yl)-2-chloro-N-(3,4-dimethoxy-phenyl)-benzamide;

N-benzothiazol-2-yl-2-chloro-N-(4-chloro-3-methoxy-phenyl)-benzamide;

N-benzothiazol-2-yl-2,4-dichloro-N-(4-chloro-3-methoxy-phenyl)-benzamide; and

N-benzothiazol-2-yl-2-chloro-4-fluoro-N-(4-chloro-3-methoxy-phenyl)-benzamide;

or a pharmaceutically acceptable salt thereof.

19. A method for the treatment of obesity in a patient in need thereof, comprising administering to said patient a compound according to claim 1 or a pharmaceutically acceptable salt thereof in an amount of from about 1 mg to 1000 mg.

20. A pharmaceutical composition comprising a therapeutically effective amount of a compound of formula (Ia)

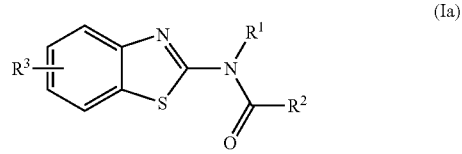

or a pharmaceutically acceptable salt thereof, wherein $R^1$ is phenyl, or phenyl mono-, di- or tri-substituted, independently, by a group selected from the group consisting of halogen, lower alkoxy, lower alkyl, halogenated-lower alkoxy and di-lower alkylamino;

$R^2$ is phenyl, or phenyl mono-, di- or tri-substituted, independently, by a group selected from the group consisting of halogen, halogenated-lower alkyl, nitro and cyano;

$R^3$ is hydrogen, lower alkyl, benzyl, lower alkoxy, cyano, nitro, amino, —$NHSO_2$—$R^{3a}$ or —NHCO—$R^{3b}$;

$R^{3a}$ is lower alkyl, di-lower alkylamino, benzyl, phenyl or phenyl mono-, di- or tri-substituted, independently, by lower alkyl;

$R^{3b}$ is benzyl, phenyl or phenyl mono-, di- or tri-substituted, independently, by lower alkyl;

provided that when $R^3$ is hydrogen, $R^1$ is selected from the group consisting of 2-halogen-phenyl, 4-lower alkoxy-phenyl, 3-lower alkyl-phenyl, 4-halogen-2-lower alkyl-phenyl, 3-halogen-2-lower alkyl-phenyl, 4-halogen-3-lower alkyl-phenyl, 2-halogen-4-lower alkyl-phenyl, 3-halogen-4-lower alkyl-phenyl, 2-lower alkoxy-4-lower alkyl-phenyl, 3-lower alkoxy-4-lower alkyl-phenyl, 4-lower alkoxy-2-lower alkyl-phenyl, 4-lower alkoxy-3-lower alkyl-phenyl, 3-lower alkoxy-2-lower alkyl-phenyl, phenyl substituted by halogenated-lower alkoxy or di-lower alkylamino, phenyl substituted by two or three groups independently selected from halogen, lower alkoxy, halogenated alkoxy and di-lower alkylamino, phenyl substituted by a lower alkyl group and one or two groups selected from halogenated alkoxy and di-lower alkylamino, and phenyl substituted by two lower alkyl groups and a group selected from halogen, lower alkoxy, halogenated alkoxy and di-lower alkylamino;

and a pharmaceutically acceptable carrier.

21. The method according to claim 19, wherein the amount is from about 1 mg to 100 mg.

* * * * *